(12) United States Patent
Domschke et al.

(10) Patent No.: US 7,927,519 B2
(45) Date of Patent: Apr. 19, 2011

(54) REFLECTION HOLOGRAM SENSOR IN CONTACT LENS

(75) Inventors: Angelika Maria Domschke, Duluth, GA (US); Xiaodong Hu, Katy, TX (US); Jian S. Zhou, Duluth, GA (US)

(73) Assignee: Eyesense AG, Basel (CH)

( * ) Notice: Subject to any disclaimer, the term of this patent is extended or adjusted under 35 U.S.C. 154(b) by 1264 days.

(21) Appl. No.: 10/564,323

(22) PCT Filed: Jun. 16, 2004

(86) PCT No.: PCT/EP2004/006492
§ 371 (c)(1),
(2), (4) Date: Aug. 3, 2006

(87) PCT Pub. No.: WO2005/015184
PCT Pub. Date: Feb. 17, 2005

(65) Prior Publication Data
US 2007/0002470 A1  Jan. 4, 2007

Related U.S. Application Data

(60) Provisional application No. 60/491,014, filed on Jul. 30, 2003.

(51) Int. Cl.
G02B 7/02 (2006.01)
(52) U.S. Cl. .................. 264/1.32; 264/1.31
(58) Field of Classification Search ............ 264/1.31, 264/1.32
See application file for complete search history.

(56) References Cited

U.S. PATENT DOCUMENTS

| | | | |
|---|---|---|---|
| 3,506,327 | A | 4/1970 | Leith et al. |
| 3,532,406 | A | 10/1970 | Hartman |
| 3,838,903 | A | 10/1974 | Leith et al. |
| 3,894,787 | A | 7/1975 | Leith et al. |
| 3,993,485 | A | 11/1976 | Chandross et al. |
| 4,312,575 | A | 1/1982 | Peyman et al. |
| 4,444,711 | A | 4/1984 | Schad |
| 4,460,534 | A | 7/1984 | Boehm et al. |
| 4,632,844 | A | 12/1986 | Yanagihara et al. |
| 5,508,317 | A * | 4/1996 | Muller ............ 522/85 |

(Continued)

FOREIGN PATENT DOCUMENTS

EP  0 655 470 B1  5/1995

(Continued)

OTHER PUBLICATIONS

Sensitive Glucose-Induced Change of the Lower Critical Solution Temperature of Poly[N,N-dimethylacrylamide-co-3-(acrylamido)phenylboronic acide] in Physiological Saline. Kataoka et al; Macromolecules 1994, 27, 1061-1062.*

*Primary Examiner* — Joseph S Del Sole
*Assistant Examiner* — Kimberly A Stewart
(74) *Attorney, Agent, or Firm* — Fanelli Haag PLLC

(57) ABSTRACT

This invention is generally related to a biocompatible sensor for detecting/measuring an analyte of interest in a body fluid and a method for making the biocompatible sensor. A biocompatible sensor of the invention comprises, consists essentially, or consists of a reflection hologram therein or thereon, wherein the reflection hologram is produced in a crosslinkable and/or polymerizable fluid material. The polymer matrix contains a molecular sensing moiety which interacts or reacts with an analyte of interest to provide an optical signal which is indicative of a change in one or more optical properties of the reflection hologram.

8 Claims, 2 Drawing Sheets

U.S. PATENT DOCUMENTS

| | | | |
|---|---|---|---|
| 5,583,163 A | 12/1996 | Müller | |
| 5,665,840 A | 9/1997 | Pöhlmann et al. | |
| 5,712,356 A | 1/1998 | Bothe et al. | |
| 5,835,245 A | 11/1998 | Robillard et al. | |
| 5,843,346 A | 12/1998 | Morrill | |
| 5,849,841 A | 12/1998 | Mühlebach et al. | |
| 5,894,002 A | 4/1999 | Boneberger et al. | |
| 5,989,923 A | 11/1999 | Lowe et al. | |
| 6,120,460 A | 9/2000 | Abreu | |
| 6,165,408 A | 12/2000 | Steinmann | |
| 6,221,303 B1 | 4/2001 | Steinmann | |
| 6,303,687 B1 | 10/2001 | Müller | |
| 6,479,587 B1 | 11/2002 | Stockinger et al. | |
| 2002/0093701 A1* | 7/2002 | Zhang et al. | 359/15 |
| 2003/0027240 A1 | 2/2003 | Asher et al. | |
| 2003/0103868 A1* | 6/2003 | Millington | 422/58 |
| 2003/0107786 A1 | 6/2003 | Bablumyan | |

FOREIGN PATENT DOCUMENTS

| | | |
|---|---|---|
| EP | 0 712 867 B1 | 5/1996 |
| EP | 0 932 635 B1 | 8/1999 |
| EP | 0 958 315 B1 | 11/1999 |
| EP | 0 961 941 B1 | 12/1999 |
| WO | WO 99/33642 A1 | 7/1999 |
| WO | WO 99/63408 A1 | 12/1999 |
| WO | WO 00/31150 A1 | 6/2000 |
| WO | WO 01/13783 A1 | 3/2001 |
| WO | WO 01/50113 A1 | 7/2001 |

* cited by examiner

REFLECTION HOLOGRAM SENSOR IN CONTACT LENS

This application is a national stage filing under 35 U.S.C. 371 of International Application No. PCT/EP2004/006492 filed Jun. 16, 2004, which claims benefits under 35 U.S.C. 119(e) of U.S. Provisional Patent Application No. 60/491,014 filed Jul. 30, 2003.

The invention is related to a method for making biocompatible sensor containing a reflection hologram. A method of the present invention is suitable for mass production of biocompatible sensors in a cost effective manner. In addition, the present invention provides biocompatible sensors and compositions for making biocompatible sensors.

BACKGROUND OF THE INVENTION

Diabetes is a serious, lifelong disease which can cause long-term complications that affect almost every part of the body. This disease often leads to blindness, heart and blood vessel disease, strokes, kidney failure, amputations, and nerve damage. Uncontrolled diabetes can complicate pregnancy, and birth defects are more common in babies born to women with diabetes. Diabetes is widely recognized as one of the leading causes of death and disability in the United States.

One important aspect in the treatment of diabetes is the tight control of blood glucose levels, which requires frequent monitoring of blood glucose levels of patients so as to manage food intake and the dosage and timing of insulin injection. Tests for determining serum glucose concentration typically require blood collection. Blood collection is an invasive technique requiring arterial or venous puncture. A patient has to endure discomfort associated with needles or other devices to obtain blood samples for testing. Currently, millions of diabetics are forced to draw blood daily to determine their blood sugar levels. In addition, blood collection sometimes can be associated with problems in various ethnic settings. To alleviate the constant discomfort and inconvenience for these individuals, substantial effort has been expanded in the search for a non-invasive or minimally invasive technology to accurately determine blood glucose levels, in particular for a non-invasive or minimally invasive to continuously or at least frequently monitor blood glucose levels.

In recent years, various non-invasive and minimally-invasive technologies have been proposed in the academic and patent literature to monitor blood glucose levels by determining glucose concentrations in an ocular fluid, such as tears, aqueous humor, or interstitial fluid. For example, PCT International Publication WO 01/13783, discloses that an ophthalmic lens comprising a chemical sensor can be used to determine the amount of an analyte (e.g., glucose) in an ocular fluid, which is accessible to light. Such chemical sensors comprise a receptor specific for an analyte of interest and a detectable label (e.g., a fluorescent label) which in combination with the receptor to provide a detectable optical signal (e.g., fluorescent signal). Fluorescent sensing system may provide a relatively high sensitivity for detecting a trace amount of an analyte of interest in a sample. However, there are some issues associated with fluorescent dyes. For instance, fluorescent dyes can be susceptible to photobleaching and therefore may not be photostable over a long period of time. Furthermore, a receptor needs to be labeled with a fluorescent label through a laborious and/or complicated process. Those issues may limit to some extend the practical application of the technologies described in WO 01/13783.

U.S. Pat. No. 6,120,460 to Abreu, in another example, suggests that a contact device containing miniaturized electrochemical sensor and placed on the front part of the eye can be used to measure glucose concentration in a tear fluid. The cost associated with miniaturization of electrochemical sensors may hinder the application of such technology.

An object of the invention is to provide an ophthalmic device, in particular, an implantable ophthalmic device, which contain a reflection hologram-based sensor for monitoring glucose levels in an ocular fluid. Such hologram-based sensor should be biocompatible and stable over a long period of time, especially when it is implanted in, on or about the eye or ocular vicinity.

Hologram-based sensors have been proposed in U.S. Pat. No. 5,989,923 and PCT International Publications WO 99/63408 and 01/50113. Those holographic chemical sensors proposed in the patent literature are largely based on a volume hologram, which is created in a silver halide-based recording material according to a process not suitable for mass, cost-effective production. Moreover, those holographic chemical sensors proposed in the patent literature may not be biocompatible so that they can not be implanted in, on or about the eye or ocular vicinity. In addition, a hologram recorded in a silver halide-based recording medium may not be stable over a long period of time, since silver halide may gradually leach out of an implantable ophthalmic device over time.

Another object of the invention is to provide a method for making a biocompatible holographic sensor. Such method can be used in large-scale, cost-effective production of biocompatible holographic sensors.

SUMMARY OF THE INVENTION

These and other objects of the invention are met by the various aspects of the invention described herein.

The invention, in one aspect, provides a method for making a biocompatible sensor containing a reflection hologram. The method comprises the steps of: introducing a crosslinkable and/or polymerizable fluid material into a cavity formed by a mold, wherein the crosslinkable and/or polymerizable fluid material comprise at least a molecular sensing moiety which can interact or react with an analyte of interest to provide an optical signal which is indicative of a change in one or more optical properties of the reflection hologram, wherein the mold has a first mold half defining a first molding surface and a second mold half defining a second molding surface, wherein said first mold half and said second mold half are configured to receive each other such that the cavity is formed between said first molding surface and said second molding surface; producing and recording a pattern of interference fringes while polymerizing/crosslinking said crosslinkable and/or polymerizable fluid material in the cavity to form the biocompatible sensor, thereby said pattern is recorded in said biocompatible sensor to form the reflection hologram.

The invention, in another aspect, provides a method for making a biocompatible sensor containing a reflection hologram. The method comprises: providing an article having a first surface and an opposite second surface; applying a coating of a crosslinkable and/or polymerizable fluid material onto at least an area on the first surface of the article, using a process selected from the group consisting of an air-assisted atomization and dispensing process, an ultrasonic-assisted atomization and dispensing process, a piezoelectric assisted atomization and dispensing process, an electro-mechanical jet printing process, a piezo-electric jet printing process, a piezo-electric with hydrostatic pressure jet printing process, and a thermal jet printing process, wherein the crosslinkable and/or polymerizable fluid material comprise at least a molecular sensing moiety which can interact or react with an analyte of interest to provide an optical signal which is indicative of a change in one or more optical properties of the reflection hologram; irradiating said coating with at least two beams of coherent light, wherein one of the two beams is directed to the coating whereas the other beam is directed to the crosslinkable and/or polymerizable fluid material through the second surface, wherein the two beams of coherent light form a pattern of interference fringes while polymerizing/crosslinking said crosslinkable and/or polymerizable fluid material in the coating to form a reflection hologram on the biocompatible sensor.

The invention, in still another aspect, provide a method for making a biocompatible sensor containing a reflection hologram. The method comprises: providing a mold, wherein the mold has a first mold half defining a first molding surface and a second mold half defining a second molding surface, wherein said first mold half and said second mold half are configured to receive each other such that a cavity is formed between said first molding surface and said second molding surface; applying a coating of a first crosslinkable and/or polymerizable fluid material onto at least one area on one of the first and second molding surfaces, using a process selected from the group consisting of an air-assisted atomization and dispensing process, an ultrasonic-assisted atomization and dispensing process, a piezoelectric assisted atomization and dispensing process, an electro-mechanical jet printing process, a piezo-electric jet printing process, a piezoelectric with hydrostatic pressure jet printing process, and a thermal jet printing process, wherein the first crosslinkable and/or polymerizable fluid material comprise at least a molecular sensing moiety which can interact or react with an analyte of interest to provide an optical signal which is indicative of a change in one or more optical properties of the reflection hologram; producing and recording a pattern of interference fringes while polymerizing/crosslinking said crosslinkable and/or polymerizable fluid material in the coating to form a reflection hologram on one of the first and second molding surfaces; introducing a second crosslinkable and/or polymerizable fluid material into the cavity formed by the mold; polymerizing/crosslinking the second crosslinkable and/or polymerizable fluid material in the cavity to form the biosensor, wherein the coating having the reflection hologram is transferred from one of the molding surfaces into the biosensor and become an integral part of the biosensor during polymerizing/crosslinking of the second crosslinkable and/or polymerizable fluid material in the cavity.

The present invention, in a still further aspect, provide a biocompatible sensor comprising a reflection hologram therein and produced according to any one of the methods of the invention.

These and other aspects of the invention will become apparent from the following description of the presently preferred embodiments. The detailed description is merely illustrative of the invention and does not limit the scope of the invention, which is defined by the appended claims and equivalents thereof. As would be obvious to one skilled in the art, many variations and modifications of the invention may be effected without departing from the spirit and scope of the novel concepts of the disclosure.

DETAILED DESCRIPTION OF PREFERRED EMBODIMENTS

Figure 1:
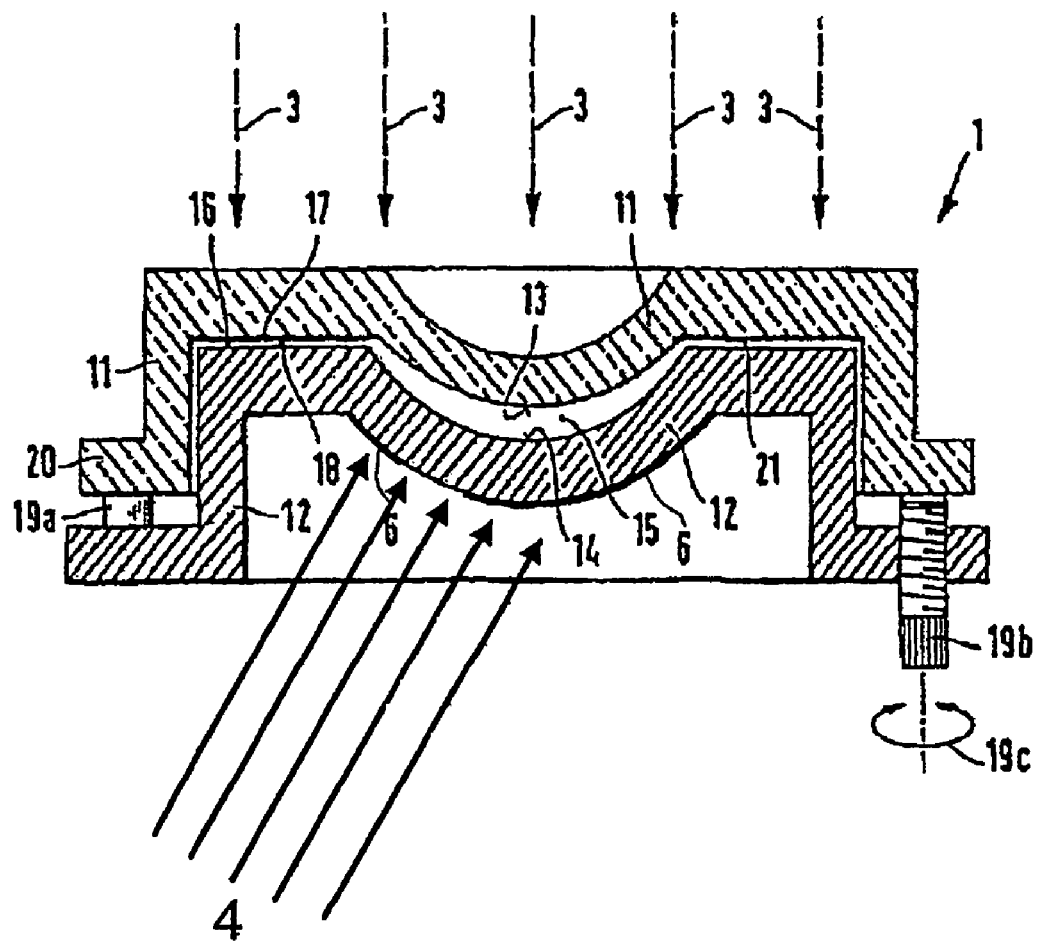
FIG. 1 schematically illustrates a setup used in a preferred method for making a biocompatible sensor with a reflection hologram.

Reference now will be made in detail to the embodiments of the invention, one or more examples of which are set forth below. Each example is provided by way of explanation of the invention, and is not a limitation of the invention. In fact, it will be apparent to those skilled in the art that various modifications and variations can be made in the present invention without departing from the scope or spirit of the invention. For instance, features illustrated or described as part of one embodiment, can be used on another embodiment to yield a still further embodiment. Thus, it is intended that the present invention covers such modifications and variations as come within the scope of the appended claims and their equivalents. Other objects, features and aspects of the present invention are disclosed in or are obvious from the following detailed description. It is to be understood by one of ordinary skill in the art that the present discussion is a description of exemplary embodiments only, and is not intended as limiting the broader aspects of the present invention.

Unless defined otherwise, all technical and scientific terms used herein have the same meaning as commonly understood by one of ordinary skill in the art to which this invention belongs. Generally, the nomenclature used herein and the laboratory procedures are well known and commonly employed in the art. Conventional methods are used for these procedures, such as those provided in the art and various general references. Where a term is provided in the singular, the inventors also contemplate the plural of that term. As employed throughout the disclosure, the following terms, unless otherwise indicated, shall be understood to have the following meanings.

The term "analyte" refers to a substance being tested. Exemplary analytes of interest include, but are not limited to, electrolytes and small molecules (e.g., sodium, potassium, chloride, phenylalanine, uric acid, galactose, glucose, cysteine, homocysteine, calcium, ethanol, acetylcholine and acetylcholine analogs, ornithine, blood urea nitrogen, creatinine), metallic elements (e.g., iron, copper, magnesium), polypeptide hormones (e.g., thyroid stimulating hormone, growth hormone, insulin, luteinizing hormones, chorionogonadotrophic hormone, obesity hormones such as leptin, serotonin and the like), chronically administered medications (e.g., dilantin, phenobarbital, propranolol), acutely administered medications (e.g., cocaine, heroin, ketamine), small molecule hormones (e.g., thyroid hormones, ACTH, estrogen, cortisol, progesterone and other metabolic steroids), markers of inflammation and/or allergy (e.g., histamine, IgE, cytokines), lipids (e.g., cholesterol, apolipo protein $A_1$), proteins and enzymes (e.g., lactoferrin, lysozyme, tear-specific prealbumin or lipocalin, albumin, complement, coagulation factors, liver function enzymes, heart damage enzymes, ferritin), markers of infection (e.g., virus components, immunoglobulins such as IgM, IgG, etc., proteases, protease inhibitors), and/or metabolites (e.g., lactate, ketone bodies).

"Biocompatible", as used herein, refers to a material or a surface of a material or an article which does not deteriorate appreciably and does not induce a significant immune response or deleterious tissue reaction, e.g., toxic reaction or significant irritation, over time when implanted into or placed adjacent to the biological tissue of a subject. Preferably, a biocompatible material does not deteriorate and does not cause immune response or deleterious tissue reaction over at least 6 months, more preferably at least 1 year, most preferably at least 10 years. Suitable biocompatible materials are highly photocrosslinkable or photopolymerizable materials. Suitable biocompatible materials include derivatives and copolymers of a polyvinyl alcohol, polyethyleneimine, or polyvinylamine. Exemplary biocompatible materials that are particularly suitable for producing a biocompatible sensor of the present invention are discussed below.

An "ophthalmic device", as used herein, refers to a contact lens (hard or soft), a corneal onlay, implantable ophthalmic devices used in, on or about the eye or ocular vicinity.

An "implantable ophthalmic device", as used herein, refers to an ophthalmic device which is used in, on or about the eye or ocular vicinity. Exemplary implantable ophthalmic devices include, without limitation, an intraocular lens, a subconjunctival lens, an intracorneal lens, and a shunt or implant (e.g., a stent, or a glaucoma shunt or the like) that can rest in the cul de sac of an eye.

The term "contact lens" employed herein in a broad sense and is intended to encompass any hard or soft lens used on the eye or ocular vicinity for vision correction, diagnosis, sample collection, drug delivery, wound healing, cosmetic appearance (e.g., eye color modification), or other ophthalmic applications.

"Ophthalmically compatible", as used herein, refers to a material or surface of a material which may be in intimate contact with the ocular environment for an extended period of time without significantly damaging the ocular environment and without significant user discomfort. Thus, an ophthalmically compatible contact lens will not produce significant corneal swelling, will adequately move on the eye with blinking to promote adequate tear exchange, will not have substantial amounts of protein or lipid adsorption, and will not cause substantial wearer discomfort during the prescribed period of wear.

"Ocular environment", as used herein, refers to ocular fluids (e.g., tear fluid) and ocular tissue (e.g., the cornea) and/or conjunctiva which may come into intimate contact with a contact lens.

A "hydrogel material" refers to a polymeric material which can absorb at least 10 percent by weight of water when it is fully hydrated. Generally, a hydrogel material is obtained by polymerization or copolymerization of at least one hydrophilic monomer in the presence of or in the absence of additional monomers and/or macromers. Exemplary hydrogels include, but are not limited to, poly(vinyl alcohol) (PVA), modified polyvinylalcohol (e.g., as nelfilcon A), poly(hydroxyethyl methacrylate), poly(vinyl pyrrolidone), PVAs with polycarboxylic acids (e.g., carbopol), polyethylene glycol, polyacrylamide, polymethacrylamide, silicone-containing hydrogels, polyurethane, polyurea, and the like. A hydrogel can be prepared according to any methods known to a person skilled in the art.

A "crosslinkable and/or polymerizable material" refers to a material which can be polymerized and/or crosslinked by actinic radiation to obtain crosslinked and/or polymerized material which are biocompatible. Examples of actinic radiation are UV irradiation, ionized radiation (e.g. gamma ray or X-ray irradiation), microwave irradiation, and the like.

A "monomer" means a low molecular weight compound that can be polymerized. Low molecular weight typically means average molecular weights less than 700 Daltons.

A "hydrophilic vinylic monomer" refers to a monomer which as a homopolymer typically yields a polymer that is water-soluble or can absorb at least 10 percent by weight water.

A "macromer" refers to medium and high molecular weight compounds or polymers that contain functional groups capable of further polymerization. Medium and high molecular weight typically means average molecular weights greater than 700 Daltons.

"Polymer" means a material formed by polymerizing one or more monomers.

A "prepolymer" refers to a starting polymer which can be polymerized and/or crosslinked upon actinic radiation to obtain a crosslinked polymer having a molecular weight much higher than the starting polymer.

"Surface modification", as used herein, means that an article has been treated in a surface treatment process (or a surface modification process), in which, by means of contact with a vapor or liquid, and/or by means of application of an energy source (1) a coating is applied to the surface of an article, (2) chemical species are adsorbed onto the surface of an article, (3) the chemical nature (e.g., electrostatic charge) of chemical groups on the surface of an article are altered, or (4) the surface properties of an article are otherwise modified. Exemplary surface treatment processes include, but are not limited to, a surface treatment by energy (e.g., a plasma, a static electrical charge, irradiation, or other energy source), chemical treatments, the grafting of hydrophilic monomers or macromers onto the surface of an article, and layer-by-layer deposition of polyelectrolytes. A preferred class of surface treatment processes are plasma processes, in which an ionized gas is applied to the surface of an article. Plasma gases and processing conditions are described more fully in U.S. Pat. Nos. 4,312,575 and 4,632,844, which are incorporated herein by reference. The plasma gas is preferably a mixture of lower alkanes and nitrogen, oxygen or an inert gas.

The term "molecular sensing moiety" employed herein in a broad sense and is intended to encompass, for example, a chemical or biochemical molecule or fragments thereof that is capable of interacting or reacting specifically with an analyte of interest in a sample to provide one or more optical signal. Exemplary molecular sensing moieties includes without limitation derivatives of phenyl boronic acid (for interacting with glucose), a receptor for specifically binding an analyte of interest, and an enzyme which reacts specifically with an anlyte of interest.

Examples of optical signals include changes in the optical properties, including, but not limited to, a change in color, changes in intensity (absorbance or reflectance) at different wavelengths, a spectral shift, and the like. A change in color can be observed by naked eyes and can be used in qualitative or semi-quantitative assays.

The term "receptor" employed herein in a broad sense and is intended to encompass, for example, a protein or fragment thereof or a biochemical compound that is capable of binding an analyte of interest in a sample. Exemplary receptors include, without limitation, antibodies or fragments thereof, lectins or fragments thereof, hormone receptors or fragments thereof, drug receptors or fragment thereof, enzymes or fragment thereof, aptamers, nucleic acids, nucleic acid analogs, and the like.

A "hologram" refers to a product of physically recording of a spatial pattern of interference fringes formed by at least two beams of coherent light, one object beam and one reference beam. The planes of interference fringes in a hologram may be flat or curved and often are termed Bragg planes. The "object beam" is the beams being modified by passing through or being reflected from an object or being designated. The "reference beam" is the beam which by-passes the object. Holograms can be classified in various ways according to the method of recording, method of reconstruction, and thickness of a recording medium. Exemplary holograms include amplitude holograms, phase holograms, thin or plane holograms, thick holograms, transmission holograms, and reflection holograms. The hologram might exist of multiple recordings varying in recording angle and plane.

"Amplitude holograms" refers to holograms that change (modulate) the amplitude of the reconstruction beam due to varying degrees of absorption in the material in a recording medium. In general, an amplitude hologram has a spatial pattern (fringes) of material with varying degrees of absorption, wherein the fringes is a physical record of an original interference pattern between at least two beams of coherent light. These holograms are also called absorption holograms.

"Phase holograms" refers to holograms that change (modulate) the phase of the reconstruction beam due to variations of the refractive index. In general, a phase hologram has a spatial pattern (fringes) of material with varying refractive index, wherein the fringes is a physical record of an original interference pattern between at least two beams of coherent light. Phase holograms can modulate a beam of light without absorbing it. As phase holograms do not absorb any energy in the material, they are brighter than amplitude holograms and also have a higher diffraction efficiency.

Amplitude and phase holograms are classified on the basis of the way the material in a recording medium modifies the incident on a hologram. It should be understood that holograms can be both amplitude and phase holograms simultaneously. For example, holograms produced on photographic emulsions (e.g., silver halides) are both amplitude and phase holograms, as the emulsion affects both phase and amplitude. It should be further understood that amplitude holograms can be converted into phase holograms. For example, standard silver halide films will respond to light by darkening through absorption of photons. The bleaching process converts the silver grains that have darkened into transparent silver halide grains. Conversion of an amplitude hologram into a phase hologram through bleaching may increase the diffraction efficiency.

"Thin holograms" refers to holograms which are produced when the thickness of a recording medium used is in the order of the wavelength of the light used.

A "thick hologram" (also called "volume hologram") refers to a hologram which is produced when the recording medium used is several wavelengths thick. Although the general classification between thin and thick holograms is made on the basis of recording medium thickness, there is no clear cut regime for plane or volume hologram. Instead there is a gradual transition in the properties of the two holograms as the recording medium thickness and the angle between object and reference beam increase. It is possible to record a plane hologram in a thick medium.

"Transmission holograms" refers to hologram that are formed by allowing the reference and object beams to enter the recording medium from the same side. Interaction of the object and reference beams in the recording medium forms fringes of material with varying refractive indices, which are approximately normal to the plane of the recording medium. When the hologram is played back by viewing with transmitted light, these fringes refract the light to produce the viewed virtual image. Such transmission holograms may be produced by methods which are well known in the art, such as disclosed in Leith and Upatnieks, U.S. Pat. Nos. 3,506,327; 3,838,903 and 3,894,787, which are herein incorporated by reference in their entireties. A diffraction grating is the simplest possible transmission hologram. It is the hologram of two coherent plane waves. It can be created by splitting a single laser beam and recombining the beams at the recording medium.

"Reflection holograms" refers to holograms which are formed by allowing the reference and object beams to enter the recording medium from opposite sides, so that they are traveling in approximately opposite directions. Interaction of the object and reference beams in the recording medium forms fringes of material with varying refractive indices, which are approximately in planes parallel to the plane of the recording medium. When the hologram is played back these fringes act as partial mirrors reflecting incident light back to the viewer. Hence, the hologram is viewed in reflection rather than in transmission. Since the wavelength selectivity of this type of hologram is very high, white light may be used for reconstruction.

Reflection holograms may be produced by an on-axis method wherein the beam of coherent radiation is projected through the recording medium onto an object therebehind. In this instance, the reflected object beam returns and intersects with the projected beam in the plane of the recording medium to form fringes substantially parallel to the plane of the medium. Reflection holograms also may be produced by an off-axis method wherein a reference beam is projected on one side of the recording medium and an object beam is projected on the reverse side of the medium. In this instance the object beam is formed by illuminating the object with coherent radiation which has not passed through the recording medium. Rather, the original beam of coherent radiation is split into two portions, one portion being projected on the medium and the other portion being directed to project on the object behind the medium. Reflection holograms produced by an off-axis process are disclosed in U.S. Pat. No. 3,532,406, which is herein incorporated by reference in its entirety.

A "holographic mirror" is the simplest reflection hologram which is formed by two beams of coherent light, none of which is modified by passing through or being reflected from an object to be imaged. A holographic mirror is the hologram of two coherent plane waves intersecting in a recording medium from substantially opposite directions. A holographic mirror can be created by splitting a single laser beam and recombining the beams at the recording medium, or the unsplit laser beam can be projected through the medium onto a plane mirror therebehind. A set of uniformly spaced fringes are formed that have a sinusoidal-like intensity distribution. The fringes are oriented parallel to the bisector of the angle between the two beams propagating in the recording medium. If the angle is 180 degree and the beams are normal to the plane of the medium, the fringes will be parallel to the plane of the medium. If the two beams do not make equal angles to the plane of the medium, then the fringes which are formed will be slanted at an acute angle relative to the plane of the medium. The holographic mirror can be characterized by its wavelength of maximum refection and by its reflection efficiency, that is, by the percent of incident radiation which is reflected at its wavelength of maximum reflection.

The term "fluid" as used herein indicates that a material is capable of flowing like a liquid.

This invention is generally related to a biocompatible sensor for detecting/measuring an analyte of interest in a body fluid and a method for making the biocompatible sensor. A biocompatible sensor of the invention comprises, consists essentially, or consists of a reflection hologram therein or thereon, wherein the reflection hologram is produced in a crosslinkable and/or polymerizable fluid material. The polymer matrix contains a molecular sensing moiety which interacts or reacts specifically with an analyte of interest to provide an optical signal which is Indicative of a change in one or more optical properties of the reflection hologram.

For example, a biocompatible sensor of the invention comprises a holographic mirror (a simplest reflection hologram) within a polymer matrix with a molecular-sensing moiety which can bind reversibly an analyte of interest. Irradiated with a white light, the holographic mirror act as a sensitive wavelength filter. The constructive interference between partial reflections from each fringe plane gives a characteristic spectral peak. The wavelength peak can be described by the Bragg equation ($\lambda$=2nD cos $\theta$, 0, D=fringe separation, n=average refractive index, $\theta$=angel of illumination). In a simplified picture, the fringes reflect a narrow bandwidth the mid-wavelength of which is approximately equal to twice the fringe spacing. When an analyte of interest enters a biocompatible sensor of the invention, it interacts or reacts specification with the sensing moiety in the polymer matrix, resulting in a change in fringe spacing which causes a shift in the peak wavelength. By spectroscopically measuring a shift in wavelength of a peak or intensities at one or more wavelengths, one can determine the concentration of an analyte of interest. Such detection can be performed preferably with a hand held device when an ophthalmic sensor of the invention is used.

Where the molecular sensing moiety is an enzyme or fragments thereof, the reaction of an analyte of interest with the enzyme will generate a number of side products. The additional number of molecules will change the fringe spacing.

Where the molecular sensing moiety is a chemical moleculae or a receptor which can specifically bind an analyte of interest, the accumulation of analyte of interest in a medium with a reflection hologram recorded therein will change the fringe spacing.

More than one hologram may be created on, or in, a biocompatible sensor of the invention. The holograms may be dimensioned and arranged so as to sense two or more independent analytes of interest.

In accordance with the present invention, a biocompatible sensor is preferably an ophthalmic ophthalmic sensor device is selected from the group consisting of a contact lens (hard or soft), a corneal onlay, implantable ophthalmic devices used in, on or about the eye or ocular vicinity.

Where an ophthalmic sensor device of the invention is a contact lens, a reflection hologram is preferably located outside of an area providing vision correction. For example, a reflection hologram can be located in an area of the lens covering the iris of an eye or near the edge of the lens. In a preferred embodiment, a reflection hologram is located in the iris area of the contact lens and can provide a cosmetic effect to a wearer.

A contact lens of the invention can be used in non-invasively monitoring of glucose levels in tears. Glucose levels in tears then can be converted into blood glucose levels based on correlations between tear glucose levels and blood glucose levels. A contact lens of the invention can be a daily-disposable contact lens, a daily-wear contact lens or an extended-wear contact lens.

Preferably, an ophthalmic sensor device is an implantable ophthalmic device. Glucose levels in tears may be much lower than blood glucose levels. With an implantable ophthalmic sensor device of the invention, one can monitor periodically or on demand glucose levels in aqueous humor or interstitial fluid where glucose levels can be much higher than glucose levels in tears. Preferably, an implantable ophthalmic sensor device of the invention is a subconjunctival implant, a stent, or a glaucoma shunt.

In accordance with the present invention, a crosslinkable and/or polymerizable fluid material is a solution of a crosslinkable and/or polymerizable material or a solvent-free liquid or melt of a crosslinkable and/or polymerizable material. A crosslinkable and/or polymerizable material can be any materials known to a skilled artisan. For example, a crosslinkable and/or polymerizable material can be a composition comprising one or more prepolymers, optionally monomers and/or macromers and optionally further including various components, such as photoinitiator, inhibitors, fillers, and the like.

A solution of a crosslinkable and/or polymerizable material can be prepared by dissolving the crosslinkable and/or polymerizable material in any suitable solvent known to a person skilled in the art. Examples of suitable solvents are water, alcohols, such as lower alkanols, for example ethanol or methanol, and furthermore carboxylic acid amides, such as dimethylformamide, dipolar aprotic solvents, such as dimethyl sulfoxide or methyl ethyl ketone, ketones, for example acetone or cyclohexanone, hydrocarbons, for example toluene, ethers, for example THF, dimethoxyethane or dioxane, and halogenated hydrocarbons, for example trichloroethane, and also mixtures of suitable solvents, for example mixtures of water with an alcohol, for example a water/ethanol or a water/methanol mixture.

A preferred group of crosslinkable and/or polymerizable materials are biocompatible, preferably ophthalmically compatible prepolymers which are water-soluble and/or meltable. It would be advantageous that a crosslinkable and/or polymerizable material comprises primarily one or more prepolymers which are preferably in a substantially pure form (e.g., purified by ultrafiltration). Therefore, after crosslinking by actinic radiation, a medical device, preferably an ophthalmic device may require practically no more subsequent purification, such as in particular complicated extraction of unpolymerized constituents. Furthermore, crosslinking may take place solvent-free or in aqueous solution, so that a subsequent solvent exchange or the hydration step is not necessary.

One example of a preferred prepolymer is a water-soluble crosslinkable poly(vinyl alcohol) prepolymer. More preferably, a water-soluble crosslinkable poly(vinyl alcohol) prepolymer is a polyhydroxyl compound which is described in U.S. Pat. Nos. 5,583,163 and 6,303,687 and has a molecular weight of at least about 2000 and which comprises from about 0.5 to about 80%, based on the number of hydroxyl groups in the poly(vinyl alcohol), of units of the formula I, I and II, I and III, or I and II and III

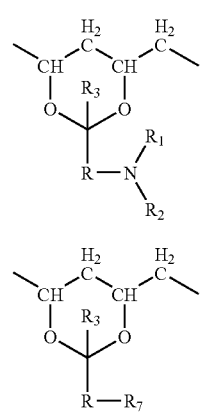

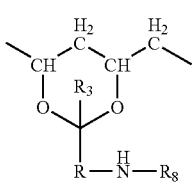

A "molecular weight", as used herein, refers to a weight average molecular weight, Mw, determined by gel permeation chromatography, unless otherwise specified.

In formula I, II and III, $R_3$ is hydrogen, a $C_1$-$C_6$ alkyl group or a cycloalkyl group.

In formula I, II and III, R is alkylene having up to 12 carbon atoms, preferably up to 8 carbon atoms, and can be linear or branched. Suitable examples include octylene, hexylene, pentylene, butylene, propylene, ethylene, methylene, 2-propylene, 2-butylene and 3-pentylene. Lower alkylene R preferably has up to 6, particularly preferably up to 4 carbon atoms. Methylene and butylene are particularly preferred.

In the formula I, $R_1$ is hydrogen or lower alkyl having up to seven, in particular up to four, carbon atoms. Most preferably, $R_1$ is hydrogen.

In the formula I, $R_2$ is an olefinically unsaturated, electron-withdrawing, crosslinkable radical, preferably having up to 25 carbon atoms. In one embodiment, $R_2$ is an olefinically unsaturated acyl radical of the formula $R_4$—CO—, in which $R_4$ is an olefinically unsaturated, crosslinkable radical having 2 to 24 carbon atoms, preferably having 2 to 8 carbon atoms, particularly preferably having 2 to 4 carbon atoms.

The olefinically unsaturated, crosslinkable radical $R_4$ having 2 to 24 carbon atoms is preferably alkenyl having 2 to 24 carbon atoms, in particular alkenyl having 2 to 8 carbon atoms, particularly preferably alkenyl having 2 to 4 carbon atoms, for example ethenyl, 2-propenyl, 3-propenyl, 2-butenyl, hexenyl, octenyl or dodecenyl. Ethenyl and 2-propenyl are preferred, so that the —CO—$R_4$ group is the acyl radical of acrylic acid or methacrylic acid.

In another embodiment, the radical $R_2$ is a radical of the formula IV, preferably of the formula V

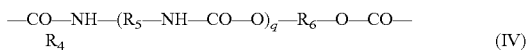

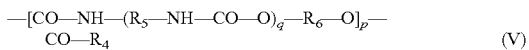

in which p and q, independently of one another, are zero or one, and $R_5$ and $R_6$, independently of one another, are lower alkylene having 2 to 8 carbon atoms, arylene having 6 to 12 carbon atoms, a saturated bivalent cycloaliphatic group having 6 to 10 carbon atoms, arylenealkylene or alkylenearylene having 7 to 14 carbon atoms or arylenealkylenearylene having 13 to 16 carbon atoms, and in which $R_4$ is as defined above.

Lower alkylene $R_5$ or $R_6$ preferably has 2 to 6 carbon atoms and is, in particular, linear. Suitable examples include propylene, butylene, hexylene, dimethylethylene and, particularly preferably, ethylene.

Arylene $R_5$ or $R_6$ is preferably phenylene, which is unsubstituted or substituted by lower alkyl or lower alkoxy, in particular 1,3-phenylene or 1,4-phenylene or methyl-1,4-phenylene.

A saturated bivalent cycloaliphatic group $R_5$ or $R_6$ is preferably cyclohexylene or cyclohexylene(lower alkylene), for example cyclohexylenemethylene, which is unsubstituted or substituted by one or more methyl groups, for example trimethylcyclohexylenemethylene, for example the bivalent isophorone radical.

The arylene unit of alkylenearylene or arylenealkylene $R_5$ or $R_6$ is preferably phenylene, unsubstituted or substituted by lower alkyl or lower alkoxy, and the alkylene unit thereof is preferably lower alkylene, such as methylene or ethylene, in particular methylene. Radicals $R_5$ or $R_6$ of this type are therefore preferably phenylenemethylene or methylenephenylene.

Arylenealkylenearylene $R_5$ or $R_6$ is preferably phenylene (lower alkylene)phenylene having up to 4 carbon atoms in the alkylene unit, for example phenyleneethylenephenylene.

The radicals $R_5$ and $R_6$ are preferably, independently of one another, lower alkylene having 2 to 6 carbon atoms, phenylene, unsubstituted or substituted by lower alkyl, cyclohexylene or cyclohexylene(lower alkylene), unsubstituted or substituted by lower alkyl, phenylene(lower alkylene), (lower alkylene)phenylene or phenylene(lower alkylene)phenylene.

In the formula II, $R_7$ is a primary, secondary or tertiary amino group or a quaternary amino group of the formula $N^+(R')_3X^-$, in which each R', independently of the others, is hydrogen or a $C_1$-$C_4$ alkyl radical and X is a counterion, for example $HSO_4^-$, $F^-$, $Cl^-$, $Br^-$, $I^-$, $CH_3COO^-$, $OH^-$, $BF^-$, or $H_2PO_4^-$.

The radicals $R_7$ are, in particular, amino, mono- or di(lower alkyl)amino, mono- or diphenylamino, (lower alkyl)phenylamino or tertiary amino incorporated into a heterocyclic ring, for example —$NH_2$, —NH—$CH_3$, —N($CH_3$)$_2$, —NH ($C_2H_5$), —N($C_2H_5$)$_2$, —NH(phenyl), —N($C_2H_5$)phenyl or

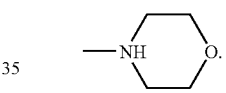

In the formula III, $R_8$ is the radical of a monobasic, dibasic or tribasic, saturated or unsaturated, aliphatic or aromatic organic acid or sulfonic acid. Preferred radicals $R_8$ are derived, for example, from chloroacetic acid, succinic acid, glutaric acid, adipic acid, pimelic acid, maleic acid, fumaric acid, itaconic acid, citraconic acid, acrylic acid, methacrylic acid, phthalic acid and trimellitic acid.

For the purposes of this invention, the term "lower" in connection with radicals and compounds denotes, unless defined otherwise, radicals or compounds having up to 7 carbon atoms, preferably having up to 4 carbon atoms.

Lower alkyl has, in particular, up to 7 carbon atoms, preferably up to 4 carbon atoms, and is, for example, methyl, ethyl, propyl, butyl or tert-butyl.

Lower alkoxy has, in particular, up to 7 carbon atoms, preferably up to 4 carbon atoms, and is, for example, methoxy, ethoxy, propoxy, butoxy or tert-butoxy.

The bivalent group —$R_5$—NH—CO—O— is present if q is one and absent if q is zero. Poly(vinyl alcohol)s containing crosslinkable groups in which q is zero are preferred.

The bivalent group —CO—NH—($R_5$—NH—CO—O)$_q$ —$R_6$—O— is present if p is one and absent if p is zero. Poly(vinyl alcohol)s containing crosslinkable groups in which p is zero are preferred.

In the poly(vinyl alcohol)s comprising units containing crosslinkable groups in which p is one, the index q is preferably zero. Particular preference is given to poly(vinyl alcohol)s comprising crosslinkable groups in which p is one, the index q is zero and $R_5$ is lower alkylene.

In the formula $N^+(R')_3X'$, $R'$ is preferably hydrogen or $C_1$-$C_3$ alkyl, and X is halide, acetate or phosphite, for example —$N^+(C_2H_5)_3CH_3COO^-$, —$N^+(C_2H_5)_3Cl^-$, and —$N^+(C_2H_5)_3H_2PO_4^-$ A water-soluble crosslinkable poly(vinyl alcohol) according to the invention is more preferably a polyhydroxyl compound which has a molecular weight of at least about 2000 and which comprises from about 0.5 to about 80%, preferably from 1 to 50%, more preferably from 1 to 25%, even more preferably from 2 to 15%, based on the number of hydroxyl groups in the poly(vinyl alcohol), of units of the formula I, wherein R is lower alkylene having up to 6 carbon atoms, $R_1$ is hydrogen or lower alkyl, $R_3$ is hydrogen, and $R_2$ is a radical of formula (V). Where p is zero, $R_4$ is preferably $C_2$-$C_8$ alkenyl. Where p is one and q is zero, $R_6$ is preferably $C_2$-$C_6$ alkylene and $R_4$ is preferably $C_2$-$C_8$ alkenyl. Where both p and q are one, $R_5$ is preferably $C_2$-$C_6$ alkylene, phenylene, unsubstituted or lower alkyl-substituted cyclohexylene or cyclo hexylene-lower alkylene, unsubstituted or lower alkyl-substituted phenylene-lower alkylene, lower alkylene-phenylene, or phenylene-lower alkylene-phenylene, $R_6$ is preferably $C_2$-$C_6$ alkylene, and $R_4$ is preferably $C_2$-$C_8$ alkenyl.

Crosslinkable poly(vinyl alcohol)s comprising units of the formula I, I and II, I and III, or I and II and III can be prepared in a manner known per se. For example, U.S. Pat. Nos. 5,583,163 and 6,303,687 disclose and teach how to prepare crosslinkable polymers comprising units of the formula I, I and II, I and III, or I and II and III.

Another example of a preferred prepolymer according to the invention is a water-soluble vinyl group-terminated polyurethane which is obtained by reacting an isocyanate-capped polyurethane with an ethylenically unsaturated amine (primary or secondary amine) or an ethylenically unsaturated monohydroxy compound. The isocyanate-capped polyurethane can be a copolymerization product of at least one polyalkylene glycol, a compound containing at least 2 hydroxyl groups, and at least one compound with two or more isocyanate groups. Preferably, the isocyanate-capped polyurethane is a copolymerization product of (a) at least one polyalkylene glycol of formula

$$HO-(R_9-O)n-(R_{10}-O)m-(R_{11}-O)l-H \quad (1)$$

wherein $R_9$, $R_{10}$, and $R_{11}$, independently of one other, are each linear or branched $C_2$-$C_4$-alkylene, and n, m and l, independently of one another, are each a number from 0 to 100, wherein the sum of (n+m+l) is 5 to 100, (b) at least one branching agent selected from the group consisting of
(i) a linear or branched aliphatic polyhydroxy compound of formula

$$R_{12}-(OH)x \quad (2),$$

wherein $R_{12}$ is a linear or branched $C_3$-$C_{18}$ aliphatic multi-valent radical and x is a number $\geq 3$,
(ii) a polyether polyol, which is the polymerization product of a compound of formula (2) and a glycol,
(iii) a polyester polyol, which is the polymerization product of a compound of formula (2), a dicarboxylic acid or a derivative thereof and a diol, and
(iv) a cycloaliphatic polyol selected from the group consisting of a C5-C8-cycloalkane which is substituted by $\geq 3$ hydroxy groups and which is unsubstituted by alkyl radical, a C5-C8-cycloalkane which is substituted by $\geq 3$ hydroxy groups and which is substituted by one or more $C_1$-$C_4$ alkyl radicals, and an unsubstituted mono- and disaccharide, (v) an aralkyl polyol having at least three hydroxy $C_1$-$C_4$ alkyl radicals, and (c) at least one di- or polyisocyanate of formula

$$R_{13}-(NCO)y \quad (3)$$

wherein $R_{13}$ a linear or branched $C_3$-$C_{24}$ aliphatic polyisocyanate, the radical of a $C_3$-$C_{24}$ cycloaliphatic or aliphatic-cycloaliphatic polyisocyanate, or the radical of a $C_3$-$C_{24}$ aromatic or araliphatic polyisocyanate, and y is a number from 2 to 6.

The isocayanate-capped polyurethane polymers according to the invention may be produced by following a solventless process. For example, in a solventless process, first one or more polyalkylene glycols of formula (1) (component (a)) is mixed with one or more branching agents (component (b)) and the mixture is heated to and maintained at a melting temperature or above. Then, at least one di- or polyisocyanate of formula (3) (component (c)) is added to the melted mixture to make a melted reaction mixture comprising component (a), component (b) and component (c) in a desired stoichiometry. The temperature of the melted reaction mixture is continuously and thoroughly stirred at the melting temperature or above and preferably under an inert atmosperic environment (for example, in nitrogen or argon atmosphere). Reaction is monitored by, for example, monitoring the isocyanate peak in FT-IR spectroscopy. Components (a)-(c) are all known compounds or compound mixtures, or may be obtained in accordance with methods known per se.

Another group of preferred prepolymers is disclosed in U.S. Pat. No. 5,849,841, which is incorporated by reference in its entirety. Suitable optical materials disclosed therein include derivatives of a polyvinyl alcohol, polyethyleneimine or polyvinylamine which contains from about 0.5 to about 80%, based on the number of hydroxyl groups in the polyvinyl alcohol or the number of imine or amine groups in the polyethyleneimine or polyvinylamine, respectively, of units of the formula VI and VII:

wherein $R^1$ and $R^2$ are, independently of one another, hydrogen, a $C_1$-$C_8$ alkyl group, an aryl group, or a cyclohexyl group, wherein these groups are unsubstitued or substituted; $R^3$ is hydrogen or a $C_1$-$C_8$ alkyl group, preferably is methyl; and $R^4$ is an —O— or —NH— bridge, preferably is —O—. Polyvinyl alcohols, polyethyleneimines and polyvinylamines suitable for the present invention have a number average molecular weight between about 2000 and 1,000,000, preferably between 10,000 and 300,000, more preferably between 10,000 and 100,000, and most preferably 10,000 and 50,000. A particularly suitable polymerizable optical material is a water-soluble derivative of a polyvinyl alcohol having between about 0.5 to about 80%, preferably between about 1 and about 25%, more preferably between about 1.5 and about 12%, based on the number of hydroxyl groups in the polyvinyl alcohol, of the formula III that has methyl groups for $R^1$ and $R^2$, hydrogen for $R^3$, —O— (i.e., an ester link) for $R^4$.

The prepolymers of the formulae VI and VII can be produced, for example, by reacting an azalactone of the formula VIII,

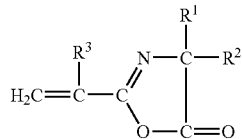

(VIII)

wherein $R^1$, $R^2$ and $R^3$ are as defined above, with a polyvinyl alcohol, polyethyleneimine or polyvinylamine at elevated temperature, between about 55° C. and 75° C., in a suitable organic solvent, optionally in the presence of a suitable catalyst. Suitable solvents are those which dissolve the polymer backbone and include aproctic polar solvents, e.g., formamide, dimethylformamide, hexamethylphosphoric triamide, dimethyl sulfoxide, pyridine, nitromethane, acetonitrile, nitrobenzene, chlorobenzene, trichloromethane and dioxane. Suitable catalyst include tertiary amines, e.g., triethylamine, and organotin salts, e.g., dibutyltin dilaurate.

A further example of a preferred prepolymer is a water-soluble crosslinkable polyurea prepolymer as described in U.S. Pat. No. 6,479,587, herein incorporated by reference in its entirety. A preferred polyurea prepolymer generally has a formula

Q-CP-Q        (4)

in which Q is an organic radical that comprises at least one crosslinkable group (carbon-carbon double bond) and CP is a bivalent copolymer fragment consisting of the segments A, B and T, provided that a segment A or B is always followed by a segment T which is followed by a segment A or B in the copolymer fragment CP and that the radical Q in formula (4) is bonded to a segment A or B.

In formula (4) the segment A is a bivalent radical of formula

—$R_{14}$N-$A_1$-N$R_{14}$'—        (5a)

in which $A_1$ is the bivalent radical of a polyalkylene glycol or is a linear or branched alkylene radical having from 2 to 24 carbon atoms and each of $R_{14}$ and $R_{14}$' independently of the other is hydrogen or unsubstituted or substituted $C_1$-$C_6$ alkyl or, in the case of the amino group that terminates the copolymer fragment, may also be a direct, ring-forming bond.

In formula (4), the segment T is a bivalent radical of formula

(5b)

in which X is a bivalent aliphatic, cycloaliphatic, aliphatic-cycloaliphatic, aromatic, araliphatic or aliphatic-heterocyclic radical.

In formula (4) the segment B is a radical of formula

—$R_{15}$N—$B_1$—N$R_{15}$'—        (5c)

in which each of $R_{15}$ and $R_{15}$' independently of the other has the meanings given above for $R_{14}$, $B_1$ is a bivalent aliphatic, cycloaliphatic, aliphatic-cycloaliphatic, aromatic or araliphatic hydrocarbon radical that is interrupted by at least one amine group of formula

(6)

in which $R_{16}$ is hydrogen, a radical Q mentioned above or a radical of formula

Q-CP'-        (7), in which Q is as defined above, and CP' is a bivalent copolymer fragment independently consisting of at least two of the above-mentioned segments A, B and T, provided that a segment A or B is always followed by a segment T which is followed by a segment A or B in the copolymer fragment CP', that the radical Q in formula (7) is bonded to a segment A or B in each case and that the N atom in formula (6) is bonded to a segment T when $R_{16}$ is a radical of formula (7).

A crosslinkable polyurea prepolymer can be obtained by reacting an acryloylchloride or an isocyanate group-containing acrylate or methacrylate with a polymerization product of $NH_2$-terminated polyalkylene glycols and di- or polyisocyanates optionally in the presence of a triamine.

Other exemplary preferred prepolymers include: crosslinkable polyacrylamide, crosslinkable statistical copolymers of vinyl lactam, MMA and a comonomer, which are disclosed in EP 655,470 and U.S. Pat. No. 5,712,356; crosslinkable copolymers of vinyl lactam, vinyl acetate and vinyl alcohol, which are disclosed in EP 712,867 and U.S. Pat. No. 5,665,840; polyether-polyester copolymers with crosslinkable side chains which are disclosed in EP 932,635; branched polyalkylene glycol-urethane prepolymers disclosed in EP 958,315 and U.S. Pat. No. 6,165,408; polyalkylene glycol-tetra(meth)acrylate prepolymers disclosed in EP 961,941 and U.S. Pat. No. 6,221,303; and crosslinkable polyallylamine gluconolactone prepolymers disclosed in PCT patent application WO 2000/31150.

In accordance with a preferred embodiment of the invention, a crosslinkable and/or polymerizable material is composed of primarily one or more prepolymers and optionally additional vinylic monomers or acrylamide monomers. Crosslinking or polymerizing is preferably effected whilst solvent-free or essentially solvent-free or directly from an aqueous solution. The prepolymer is preferably in a substantially pure form, for example, as obtained by a purification step, such as ultrafiltration. For example, crosslinking or polymerizing may be undertaken from an aqueous solution containing about 15 to 90% of one or more prepolymers.

The vinylic monomer which may be additionally used for photo-crosslinking or polymerizing in accordance with the invention may be hydrophilic, hydrophobic or may be a mixture of a hydrophobic and a hydrophilic vinylic monomer. Suitable vinylic monomers include especially those normally used for the manufacture of contact lenses. A "hydrophilic vinylic monomer" refers to a monomer which as a homopolymer typically yields a polymer that is water-soluble or can absorb at least 10 percent by weight water. A "hydrophobic vinylic monomer" refers to a monomer which as a homopolymer typically yields a polymer that is insoluble in water and can absorb less than 10 percent by weight water.

It is preferable to use a hydrophobic vinylic monomer, or a mixture of a hydrophobic vinylic monomer with a hydrophilic vinylic monomer, whereby this mixture contains at least 50 percent by weight of a hydrophobic vinyl comonomer. In this way, the mechanical properties of the resultant polymer may be improved without the water content dropping substantially. Both conventional hydrophobic vinylic monomers and conventional hydrophilic vinylic monomers are suitable for copolymerization with the prepolymers.

Suitable hydrophobic vinylic monomers include, without limitation, $C_1$-$C_{18}$-alkylacrylates and -methacrylates, $C_3$-$C_{18}$ alkylacrylamides and -methacrylamides, acrylonitrile, methacrylonitrile, vinyl-$C_1$-$C_{18}$-alkanoates, $C_2$-$C_{18}$-alkenes, $C_2$-$C_{18}$-halo-alkenes, styrene, $C_1$-$C_6$-alkylstyrene, vinylalkylethers in which the alkyl moiety has 1 to 6 carbon atoms, $C_2$-$C_{10}$-perfluoroalkyl-acrylates and -methacrylates or correspondingly partially fluorinated acrylates and methacrylates, $C_3$-$C_{12}$-perfluoroalkyl-ethyl-thiocarbonylaminoethyl-acrylates and -methacrylates, acryloxy and -methacryloxy-alkylsiloxanes, N-vinylcarbazole, $C_1$-$C_{12}$-alkylesters of maleic acid, fumaric acid, itaconic acid, mesaconic acid and the like. Preference is given e.g. to $C_1$-$C_4$-alkylesters of vinylically unsaturated carboxylic acids with 3 to 5 carbon atoms or vinylesters of carboxylic acids with up to 5 carbon atoms.
Suitable hydrophilic vinylic monomers include, without limitation, hydroxy-substituted lower alkylacrylates and -methacrylates, acrylamide, methacrylamide, lower alkyl-acrylamides and -methacrylamides, ethoxylated acrylates and methacrylates, hydroxy-substituted lower alkyl-acrylamides and -methacrylamides, hydroxy-substituted lower alkylvinyl-ethers, sodium ethylene sulphonate, sodium styrene sulphonate, 2-acrylamido-2-methyl-propane-sulphonic acid, N-vinyl pyrrole, N-vinyl succinimide, N-vinyl pyrrolidone, 2- or 4-vinyl pyridine, acrylic acid, methacrylic acid, amino- (whereby the term "amino" also includes quaternary ammonium), mono-lower-alkylamino- or di-lower-alkylamino-lower-alkyl-acrylates and -methacrylates, allyl alcohol and the like. Preference is given e.g. to hydroxy-substituted $C_2$-$C_4$-alkyl(meth)acrylates, five- to seven-membered N-vinyl-lactams, N,N-di-$C_1$-$C_4$-alkyl-methacrylamides and vinylically unsaturated carboxylic acids with a total of 3 to 5 carbon atoms.

Preferred hydrophobic vinylic monomers are methyl methacrylate and vinyl acetate. Preferred hydrophilic vinylic comonomers are 2-hydroxyethyl methacrylate, N-vinyl pyrrolidone and acrylamide.

To facilitate the photocrosslinking and/or polymerizing process, it is desirable to add a photoinitiator, which can initiate radical crosslinking and/or polymerizing. Exemplary photoinitators suitable for the present invention include benzoin methyl ether, 1-hydroxycyclohexylphenyl ketone, Durocure® 1173 and Irgacure® photoinitators. Preferably, between about 0.3 and about 2.0%, based on the total weight of the polymerizable formulation, of a photoinitiator is used.

As is known in the holographic art, as the refractive index modulation increases, the optical signal intensity from a hologram increases. Accordingly, it is desirable to increase the refractive index of the material used in the recording medium for recording a hologram. For such purpose, nano particles with high refractive index can be incorporated in a crosslinkable and/or polymerizable fluid material for making a biocompatible sensor of the invention. Nano particles can be inorganic nano particles and colloids.

In accordance with the present invention, a crosslinkable and/or polymerizable fluid material is capable of transferring energy modulation into material density modulation, which subsequently results in the desired refractive index modulation.

In accordance with a preferred embodiment of the present invention, a crosslinkable and/or polymerizable material comprises one or more refractive index enhancing modifiers which can be attached to the backbone of a polymer matrix derived from the crosslinkable and/or polymerizable material. Exemplary refractive index enhancing modifiers includes aromatic groups which can be present either in a vinylic monomer and/or in a prepolymer. The introduction of aromatic groups into the polymer matrix, increases the overall refractive index of the matrix which leads to increase refractive index differences [delta n] between areas of different polymer densities. Additional increase in delta n is resulted from aromate/polymer interactions, which enhance the packing order of the polymer chains in high density areas, thereby enhancing achievable efficiency of polymer. Areas of different polymer densities are caused by different irradiations resulted from the pattern of interference fringes.

In another preferred embodiment, a crosslinkable and/or polymerizable fluid material is an aqueous solution of one or more prepolymers and optionally one or more vinylic monomers, wherein the aqueous solution includes low molecular weight additives, such as NaCl, which exhibit a limited compatibility with a polymer resulted from the crosslinkable and/or polymerizable fluid material, but good compatibility with water. By virtue of the limited compatibility, the additive causes an osmotic gradient, which induces a contraction of a resulting polymer matrix. It is believed that the additive separates during the hologram recording period from areas of high irradiation intensity, in which the polymerizing and/or crosslinking process is initiated, into areas of low irradiation intensity. Such separation causes an osmotic gradient, followed by localized dehydration and contraction of the resulting polymer matrix. As a consequence, refractive index differences [delta n] between high and low irradiated areas increase and high efficiency materials are obtained. High and low irradiated areas are resulted from the pattern of interference fringes. NaCl is a component of the lens storage solution and thus no extraction process is necessary during the lens preparation process.

A molecular sensing moiety can be physically bond or covalently linked to a polymer matrix prepared from a crosslinkable and/or polymerizable fluid material, according to any known, suitable methods. For example, a prepolymer and a molecular sensing compound, which comprises or be modified to comprise matching functional groups, can be covalently linked with each other, thereby incorporating molecular sensing moiety into the modified prepolymer.

It is well known in the art that a pair of matching functional groups can form a covalent bond or linkage under known reaction conditions, such as, oxidation-reduction conditions, dehydration condensation conditions, addition conditions, substitution (or displacement) conditions, 2+2 cyclo-addition conditions, Diels-Alder reaction conditions, ROMP (Ring Opening Metathesis Polymerization) conditions, vulcanization conditions, cationic crosslinking conditions, and epoxy hardening conditions. For example, an amino group is covalently bondable with aldehyde (Schiff base which is formed from aldehyde group and amino group may further be reduced); an hydroxyl group and an amino group are covalently bondable with carboxyl group; carboxyl group and a sulfo group are covalently bondable with hydroxyl group; or a mercapto group is covalently bondable with amino group.

Exemplary covalent bonds or linkage, which are formed between pairs of crosslinkable groups, include without limitation, ester, ether, acetal, ketal, vinyl ether, carbamate, urea, amine, amide, enamine, imine, oxime, amidine, iminoester, carbonate, orthoester, phosphonate, phosphinate, sulfonate, sulfinate, sulfide, sulfate, disulfide, sulfinamide, sulfonamide, thioester, aryl, silane, siloxane, heterocycles, thiocarbonate, thiocarbamate, and phosphonamide.

Exemplary functional groups include hydroxyl group, amine group, amide group, sulfhydryl group, —COOR (R and R' are hydrogen or $C_1$ to $C_8$ alkyl groups), halide (chloride, bromide, iodide), acyl chloride, isothiocyanate, isocyanate, monochlorotriazine, dichlorotriazine, mono- or di-halogen substituted pyridine, mono- or di-halogen substituted diazine, phosphoramidite, maleimide, aziridine, sulfonyl halide, hydroxysuccinimide ester, hydroxysulfosuccinimide ester, imido ester, hydrazine, axidonitrophenyl group, azide, 3-(2-pyridyl dithio)proprionamide, glyoxal, aldehyde, epoxy.

It is understood that coupling agents may be used. Coupling agents useful for coupling antimicrobial peptide to the LbL coating of a medical device include, without limitation, N. N'-carbonyldiimidazole, carbodiimides such as 1-ethyl-3-(3-dimethylaminopropyl)carbodiimide ("EDC"), dicyclohexyl carbodiimide, 1-cylcohexyl-3-(2-morpholinoethyl) carbodiimide, diisopropyl carbodiimide, or mixtures thereof. The carbodiimides also may be used with N-hydroxysuccinimide or N-hydroxysulfosuccinimide to form esters that can react with amines to form amides.

Alternatively, a molecular sensing moiety can be incorporated in a vinylic monomer which is one of the components of a crosslinkable and/or polymerizable fluid material.

A molecular sensing compound can also be copolymerized with a hydrogel forming nano- or micro-particles, which can be implemented into the matrix.

Any known suitable molecular sensing moieties can be used in the present invention. For example, if glucose is an analyte of interest to be detected, the molecular sensing moiety preferably are derivatives of phenyl boronic acid, concanavalin A, a deactivated glucose oxidase, hexokinase or glucosegalactose binding protein also can be used.

Examples of preferred derivatives of phenyl boronic acid include, without limitation, those having the following structural formula:

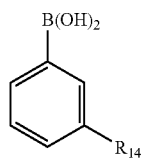

(4)

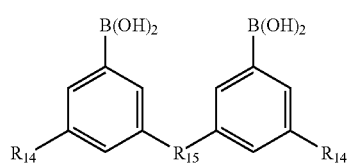

(5)

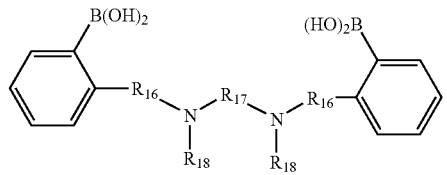

(6)

It is understood that the phenyl ring of a derivative of phenyl boronic acid can be substituted with electron withdrawing groups such as fluorine or nitrate and that the position of the boronic acid may vary.

In formula (4)-(6), $R_{14}$ and $R_{18}$, independently of each other, are olefinically unsaturated, crosslinkable radicals, preferably having up to 25 carbon atoms.

In formula (4)-(6), $R_{15}$ and $R_{16}$, independently of each other, are alkylene having up to 12 carbon atoms, preferably up to 8 carbon atoms, and can be linear or branched. Suitable examples include octylene, hexylene, pentylene, butylene, propylene, ethylene, methylene, 2-propylene, 2-butylene and 3-pentylene. Lower alkylene $R_{15}$ and $R_{16}$ preferably has up to 6, particularly preferably up to 4 carbon atoms. Methylene and butylene are particularly preferred.

In formula (4)-(6), $R_{17}$ is an arylene having 6 to 12 carbon atoms, a saturated bivalent cycloaliphatic group having 6 to 10 carbon atoms, arylenealkylene or alkylenearylene having 7 to 14 carbon atoms or arylenealkylenearylene having 13 to 16 carbon atoms.

Arylene $R_{17}$ is preferably phenylene, which is unsubstituted or substituted by lower alkyl or lower alkoxy, in particular 1,3-phenylene or 1,4-phenylene or methyl-1,4-phenylene.

A saturated bivalent cycloaliphatic group $R_{17}$ is preferably cyclohexylene or cyclohexylene(lower alkylene), for example cyclohexylenemethylene, which is unsubstituted or substituted by one or more methyl groups, for example trimethylcyclohexylenemethylene, for example the bivalent isophorone radical.

The arylene unit of alkylenearylene or arylenealkylene $R_{17}$ is preferably phenylene, unsubstituted or substituted by lower alkyl or lower alkoxy, and the alkylene unit thereof is preferably lower alkylene, such as methylene or ethylene, in particular methylene. Radicals $R_{17}$ of this type are therefore preferably phenylenemethylene or methylenephenylene.

Arylenealkylenearylene $R_{17}$ is preferably phenylene(lower alkylene)phenylene having up to 4 carbon atoms in the alkylene unit, for example phenyleneethylenephenylene.

One example of a derivative of phenyl boronic acid having formula (4) is 3-acrylamido phenylboronate (3-APB), wherein $R_{14}$ is

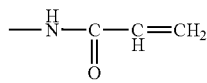

A derivative of phenyl boronic acid having formula (4), (5) or (6) can be incorporated in a crosslinkable and/or polymerizable fluid material for making a biocompatible glucose sensor.

It is also preferred that a polydiacetylene modified with boronic acids is incorporated in a crosslinkable and/or polymerizable fluid material for making a biocompatible glucose sensor. It is believed that upon attachment of the glucose to the boronic acid a sudden confirmation change of the polydiacetylene occurs, thereby causing changes in fringe spacing as well as a color change. A preferred polydiacetylene modified with boronic acids has formula (7)

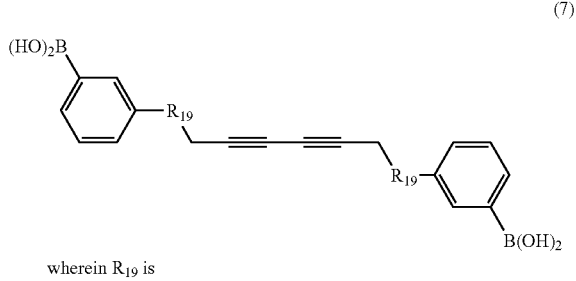
(7)

wherein $R_{19}$ is

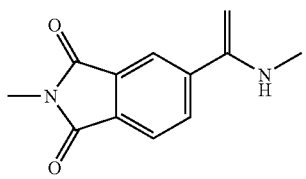

In order to increase the wavelength shift and thus the response to the analyte, the fringes can be contracted prior to the expansion by the analyte. This contraction can be introduced by a conjugate between receptor moiety and a matrix tethered competitive binding moiety, which will be replaced by the analyte. For example, a crosslinkable and/or polymerizable fluid material can comprises a prepolymer, 3-acrylamido phenylboronate (3-APB) and polymerizable and/or crosslinkable dextran.

Other side products may cause changes in pH which also lead to fringe modulation caused by the swelling of the matrix material. The swelling behavior on pH modulation can be enhanced by the introduction of chargeable groups (such as carboxylic groups, sulfonic acid groups) into the polymer matrix.

On the other hand the introduction of certain protonated groups (such as aminogroups) which will deprotonate on pH increase can be used to enhance the contraction of the fringes prior to the expansion by the analyte reaction.

Competitive solvation strengths between certain low molecular weight molecules and the PVA matrix in water can also be used to introduce contraction or expansion.

An implantable opththalmic sensor of the invention can found particular use in measuring the concentration of an analyte, especially glucose, in intertissual fluids. A non-implantable ophthalmic sensor such as a contact lens can find particular use in non-invasive monitoring of glucose concentration in an ocular fluid.

An ophthalmic sensor of the invention can also be a disposable strip, which is only temporally in contact with an ocular fluid and taken out for the detection of the analyte. Such disposable strip preferably is made of a hydrogel material and in a substantially dry state. By contacting with an ocular fluid (e.g., tear), the substantially dry strip can absorb the ocular fluid and facilitate the measurement or detection of an analyte of interest.

It is also preferred that a crosslinkable and/or polymerizable fluid material for making an implantable sensor of the invention can form porous polymer matrix which will allow a free flow of nutritions through the matrix.

It should be understood that a crosslinkable and/or pblymerizable fluid material can also contain silver halides and other conventional holographic optical element recording media.

The invention, in one aspect, provides a method for making a biocompatible sensor containing a reflection hologram. The method comprises the steps of: introducing a crosslinkable and/or polymerizable fluid material into a cavity formed by a mold, wherein the crosslinkable and/or polymerizable fluid material comprise at least a molecular sensing moiety which can interact or react with an analyte of interest to provide an optical signal which is indicative of a change in one or more optical properties of the reflection hologram, wherein the mold has a first mold half defining a first molding surface and a second mold half defining a second molding surface, wherein said first mold half and said second mold half are configured to receive each other such that the cavity is formed between said first molding surface and said second molding surface; producing and recording a pattern of interference fringes while polymerizing/crosslinking said crosslinkable and/or polymerizable fluid material in the cavity to form the blocompatible sensor, thereby said pattern is recorded in said biocompatible sensor to form the reflection hologram.

The step of producing and recording can be carried according to one of two approaches.

In the first approach, at least two beams of coherent light can be used to produce and record a pattern of interference fringes while polymerizing/crosslinking a crosslinkable and/or polymerizable fluid material to form a biocompatible sensor. The pattern is recorded in said biocompatible sensor to form a reflection hologram. One of the two beams is directed to the crosslinkable and/or polymerizable fluid material through the first molding surface whereas the other beam is directed to the crosslinkable and/or polymerizable fluid material through at least a portion of the second molding surface.

In the second approach, one single beam can be used to produce and record a pattern of interference fringes while polymerizing/crosslinking a crosslinkable and/or polymerizable fluid material to form a biocompatible sensor. In accordance with this approach, one of the two mold halves, for example, the second mold half, has on or behind it molding surface, a mirror to reflect a coming light. By directing an incident beam of coherent light to a crosslinkable and/or polymerizable fluid material through the first molding surface, wherein the incident beam and a beam reflected by the mirror form a pattern of interference fringes while polymerizing/crosslinking the crosslinkable and/or polymerizable fluid material to form a biocompatible sensor, thereby the pattern is recorded in the biocompatible sensor to form a reflection hologram.

FIG. 1 schematically illustrated a preferred process for producing an ophthalmic lens containing a reflection hologram from a liquid crosslinkable and/or polymerizable fluid material in a mold 1.

The mold 1 consists of two mold halves 11 and 12, each having a curved molding surface 13 and 14 which together define a mold cavity 15, which in turn determines the shape of the lens to be manufactured. The mold cavity 15 can be completely and tightly closed, but in the embodiment illustrated is open around its peripheral edge which defines the edge of the lens to be manufactured, and is linked to a relatively narrow annular gap 16. The annular gap 16 is limited or formed by a flat mold wall 17 and 18 on each of the two mold halves 11 and 12. In order to prevent complete closure of the mold, spacers, for example in the form of several bolts 19a or 19b, are provided on the mold 12, and these interact with a collar or flange 20 of the mould 11 and keep the two mold halves at such a distance apart that the said annular gap 16 results. As is indicated symbolically in FIG. 1 by the right-hand spacer bolt 19b with a thread, the spacers may also be of adjustable or spring-action formation. In this way, the two mold halves 11, 12 can be moved towards one another during the crosslinking process to balance out leakage, by adjusting the spacers (indicated symbolically by the arrow 19c showing the direction of rotation) or against a spring action. Of course, the mold can be opened and closed in the usual manner, for example by means of a closure unit (not shown). Adjustment of the gap between the two mold halves 11, 12 to balance out leakage, may also be effected e.g. using this external closure unit.

It is also conceivable that, instead of the continuous annular gap 16 and the spacers 19a and 19b, a series of segmentous gaps may be provided, the intermediate areas between the individual segment gaps taking over the function of the spacers. Of course, other configurations of mold halves are also conceivable.

On the mold wall 17 in the area of the annular gap 16, there is a mask 21 which is impermeable to UV light, (or a mask which at least has poor permeability compared with the permeability of the mold), and this mask extends right to the mold cavity 15, and with the exception of the same, screens all the other parts, hollow spaces or areas of the mold 1 that are in contact with or may come into contact with the liquid, uncrosslinked, possibly excess material, from irradiation. Partial areas of the lens edge are therefore formed not by a limitation of the material by mold walls, but by a spatial limitation of the radiation triggering polymerisaton or crosslinking.

In the case of UV light, the mask 21 may be preferably a chromium layer, that can be produced by processes known e.g. from photography or UV-lithography. The mask 21 does not necessary have to be fixed; it may also be, for example, removable or exchangeable.

The external surface of the mold 12 is covered by a mask 6, which is impermeable to UV light. A reference beam of light 4 can only pass through a portion of the molding surface 14 to irradiate the crosslinkable and/or polymerizable fluid material.

An objection beam of light 3 and a reference beam of light 4 simultaneously irradiates the crosslinkable and/or polymerizable fluid material in the cavity 15. Preferably, the object beam and the reference beam are produced from one light source, using a beamspliter. The object beam 3 and reference beam 4 forms interference fringe patterns, which are recorded in the crosslinkable and/or polymerizable fluid material as it is polymerized and/or crosslinked, thereby forming a reflection hologram. In the embodiment illustrated, irradiation of the reference beam 4 is spatially limited by a mask 6 which is impermeable to the irradiation and therefore the reflection hologram is recorded only in a spatially limited area of the crosslinkable and/or polymerizable fluid material.

Figure 2:
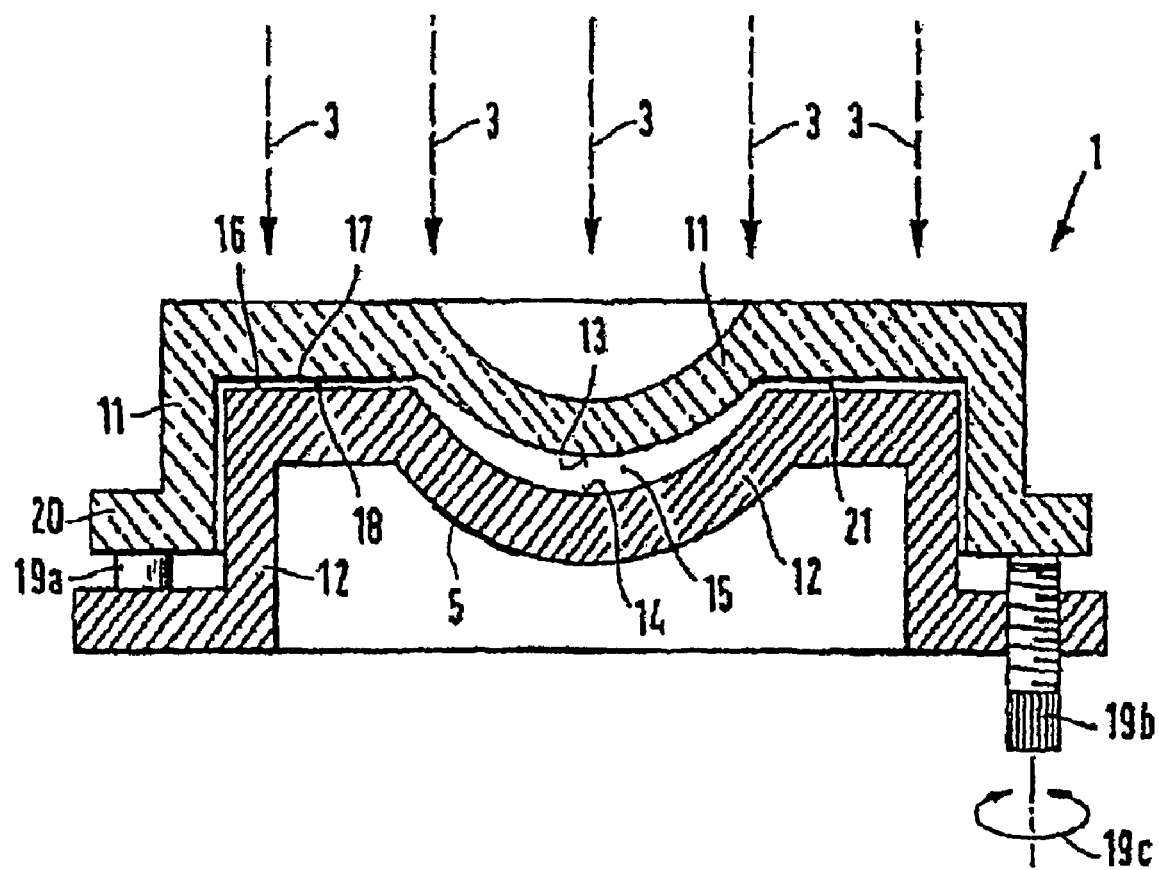
FIG. 2 schematically illustrates a setup used in a preferred method for making a biocompatible sensor with a reflection hologram.

FIG. 2 schematically illustrated a preferred process for producing an ophthalmic lens containing a reflection hologram from a liquid crosslinkable and/or polymerizable fluid material in a mold 1.

The mold 1 consists of two mold halves 11 and 12, each having a curved molding surface 13 and 14 which together define a mold cavity 15, which in turn determines the shape of the lens to be manufactured. The mold cavity 15 can be completely and tightly closed, but in the embodiment illustrated is open around its peripheral edge which defines the edge of the lens to be manufactured, and is linked to a relatively narrow annular gap 16. The annular gap 16 is limited or formed by a flat mold wall 17 and 18 on each of the two mold halves 11 and 12. In order to prevent complete closure of the mold, spacers, for example in the form of several bolts 19a or 19b, are provided on the mold 12, and these interact with a collar or flange 20 of the mould 11 and keep the two mold halves at such a distance apart that the said annular gap 16 results. As is indicated symbolically in FIG. 2 by the right-hand spacer bolt 19b with a thread, the spacers may also be of adjustable or spring-action formation. In this way, the two mold halves 11, 12 can be moved towards one another during the crosslinking process to balance out leakage, by adjusting the spacers (indicated symbolically by the arrow 19c showing the direction of rotation) or against a spring action. Of course, the mold can be opened and closed in the usual manner, for example by means of a closure unit (not shown). Adjustment of the gap between the two mold halves 11, 12 to balance out leakage, may also be effected e.g. using this external closure unit.

It is also conceivable that, instead of the continuous annular gap 16 and the spacers 19a and 19b, a series of segmentous gaps may be provided, the intermediate areas between the individual segment gaps taking over the function of the spacers. Of course, other configurations of mold halves are also conceivable.

On the mold wall 17 in the area of the annular gap 16, there is a mask 21 which is impermeable to UV light, (or a mask which at least has poor permeability compared with the permeability of the mold), and this mask extends right to the mold cavity 15, and with the exception of the same, screens all the other parts, hollow spaces or areas of the mold 1 that are in contact with or may come into contact with the liquid, uncrosslinked, possibly excess material, from irradiation. Partial areas of the lens edge are therefore formed not by a limitation of the material by mold walls, but by a spatial limitation of the radiation triggering polymerisation or crosslinking.

In the case of UV light, the mask 21 may be preferably a chromium layer, that can be produced by processes known e.g. from photography or UV-lithography. The mask 21 does not necessary have to be fixed; it may also be, for example, removable or exchangeable.

The mold half 12 has a mirror 5 located on its external surface opposite of the molding surface 14. When an object beam 3 of light illuminate the mirror 5, it will be reflected back. The reflected beam of light acts as a reference beam of light and forms interference fringe patterns with the object beam 3. The interference fringe patterns are recorded in the crosslinkable and/or polymerizable fluid material as it is polymerized and/or crosslinked, thereby forming a reflection hologram.

In a preferred embodiment, the crosslinkable and/or polymerizable fluid material can be first partially polymerized and/or crosslinked, for example, by a very short duration of UV irradiation, prior to the irradiation with the object and reference lights. By partially crosslinking and/or polymerizing, the crosslinkable and/or polymerizable fluid material can become more viscous or quasi-solidified. Partial crosslinking and/or polymerizing can be achieved by adjusting the duration of irradiation or energy levels of irradiation. A person skilled in the art will be able to determine the conditions under which a crosslinkable and/or polymerizable fluid material can be partially polymerized and/or crosslinked in a way that the crosslinkable and/or polymerizable fluid material become viscous or quasi-solidified in a mold.

Methods of manufacturing mold halves for cast molding of an ophthalmic lens are generally well known to those of ordinary skill in the art. The process of the present invention is not limited to any particular method of forming a mold. In fact, any method of forming a mold can be used in the present invention. Examples of suitable processes for forming the mold halves are disclosed in U.S. Pat. No. 4,444,711 to Schad; U.S. Pat. No. 4,460,534 to Boehm et al.; U.S. Pat. No. 5,843,346 to Morril; and U.S. Pat. No. 5,894,002 to Boneberger et al., which are also incorporated herein by reference.

A mold can be disposable or re-usable. Virtually all materials known in the art for making molds can be used. Examples of materials for making molds include, without limitation, quartz/glass, polyethylene, polypropylene, polystyrene (PS), polymethylmethacrylate (PMMA), polyacrylonitrile (PA), methacrylate/acrylonitrile copolymer (MAN), Luran 368R (styrene/acrylonitrile copolymer, SAN), Terlux KR-2812 (methyl-methacrylate/acrylonitrile/butadiene/styrene polymer, MABS), Topas from the company Ticono, CR-39 (chemically crosslinked polymer consisting of allyl diglycol carbonate monomer), PMMA GS-222 from the company Röhm, Goldflex (GF), Delrin (DR), and Barex 210 (methacrylate/acrylonitrile polymer, MAN). UV-transmissive and/or UV-opaque materials can also be used. One such material that passes ultraviolet light is, for instance, polymethylmethacrylate (PMMA). In one embodiment, one portion of the mold is formed from a UV transmissive material, such as polymethylacrylate, so that UV light can later pass through the section to cure a polymerizable material dispensed within the mold. In another embodiment, another portion of the mold is formed from a UV-opaque material that blocks UV light.

The invention, in another aspect, provide a method for making a biocompatible sensor containing a reflection hologram. The method comprises: providing a mold, wherein the mold has a first mold half defining a first molding surface and a second mold half defining a second molding surface, wherein said first mold half and said second mold half are configured to receive each other such that a cavity is formed between said first molding surface and said second molding surface; applying a coating of a first crosslinkable and/or polymerizable fluid material onto at least one area on one of the first and second molding surfaces, using a process selected from the group consisting of an air-assisted atomization and dispensing process, an ultrasonic-assisted atomization and dispensing process, a piezoelectric assisted atomization and dispensing process, an electro-mechanical jet printing process, a piezo-electric jet printing process, a piezoelectric with hydrostatic pressure jet printing process, and a thermal jet printing process, wherein the first crosslinkable and/or polymerizable fluid material comprise at least a molecular sensing moiety which can interact or react with an analyte of interest to provide an optical signal which is indicative of a change in one or more optical properties of the reflection hologram; producing and recording a pattern of interference fringes while polymerizing/crosslinking said crosslinkable and/or polymerizable fluid material in the coating to form a reflection hologram on one of the first and second molding surfaces; introducing a second crosslinkable and/or polymerizable fluid material into the cavity formed by the mold; polymerizing/crosslinking the second crosslinkable and/or polymerizable fluid material in the cavity to form the biosensor, wherein the coating having the reflection hologram is transferred from one of the molding surfaces into the biosensor and become an integral part of the biosensor during polymerizing/crosslinking of the second crosslinkable and/or polymerizable fluid material in the cavity.

The first and second crosslinkable and/or polymerizable fluid material can comprises identical prepolymers or different prepolymers. Preferably, the first and second crosslinkable and/or polymerizable fluid material.

The coating on the molding surface of one of the two mold halves can have any desired thickness.

To facilitate transferring of the coating from the molding surface of one of the two mold halves into a resultant biosensor during curing process of the second crosslinkable and/or polymerizable fluid material in the mold cavity, it may be desirable to apply a releasing agent before applying the coating of the first crosslinkable and/or polymerizable fluid material. Any releasing agent known to a person skilled in the art can be used.

The invention, in still another aspect, provides a method for making a biocompatible sensor containing a reflection hologram. The method comprises: providing an article having a first surface and an opposite second surface; applying a coating of a crosslinkable and/or polymerizable fluid material onto at least an area on the first surface of the article, using a process selected from the group consisting of an air-assisted atomization and dispensing process, an ultrasonic-assisted atomization and dispensing process, a piezoelectric assisted atomization and dispensing process, an electro-mechanical jet printing process, a piezo-electric jet printing process, a piezoelectric with hydrostatic pressure jet printing process, and a thermal jet printing process, wherein the crosslinkable and/or polymerizable fluid material comprise at least a molecular sensing moiety which can interact or react with an analyte of interest to provide an optical signal which is indicative of a change in one or more optical properties of the reflection hologram; irradiating said coating with at least two beams of coherent light, wherein one of the two beams is directed to the coating whereas the other beam is directed to the crosslinkable and/or polymerizable fluid material through the second surface, wherein the two beams of coherent light form a pattern of interference fringes while polymerizing/crosslinking said crosslinkable and/or polymerizable fluid material in the coating to form a reflection hologram on the biocompatible sensor.

In a preferred embodiment, the process comprises a step of evaporating partially or completely a solvent of the crosslinkable and/or polymerizable fluid material, or a step of partially polymerizing and/or crosslinking the crosslinkable and/or polymerizable fluid material, before the step of irradiating. As described above, partial crosslinking and/or polymerizing can be achieved by adjusting the duration of irradiation or energy levels of irradiation.

The present invention in a further aspect, provide a biocompatible sensor comprising a reflection hologram therein and produced according to any one of the methods described above.

The present invention, in a still further aspect, provides a fluid composition for making a biocompatible sensor with a reflection hologram therein. The composition comprises at least one prepolymer, optionally a vinylic monomer, and a molecular sensing moiety associated with the prepolymer or vinylic monomer, wherein the prepolymer is selected from the group consisting of: a water-soluble crosslinkable poly (vinyl alcohol) prepolymer; a water-soluble vinyl group-terminated polyurethane; water-soluble crosslinkable derivatives of a polyvinyl alcohol; water-soluble crosslinkable derivatives of a polyethyleneimine; water-soluble crosslinkable derivatives of a polyvinylamine; a water-soluble crosslinkable polyurea prepolymer; crosslinkable statistical copolymers of vinyl lactam, MMA and a comonomer, which are disclosed in EP 655,470 and U.S. Pat. No. 5,712,356; crosslinkable copolymers of vinyl lactam, vinyl acetate and vinyl alcohol, which are disclosed in EP 712,867 and U.S. Pat. No. 5,665,840; polyether-polyester copolymers with crosslinkable side chains which are disclosed in EP 932,635;

branched polyalkylene glycol-urethane prepolymers disclosed in EP 958,315 and U.S. Pat. No. 6,165,408; polyalkylene glycol-tetra(meth)acrylate prepolymers disclosed in EP 961,941 and U.S. Pat. No. 6,221,303; and crosslinkable polyallylamine gluconolactone prepolymers disclosed in PCT patent application WO 2000/31150.

Preferred examples of a water-soluble crosslinkable poly(vinyl alcohol) prepolymer, a water-soluble vinyl group-terminated polyurethane, water-soluble crosslinkable derivatives of a polyvinyl alcohol, water-soluble crosslinkable derivatives of a polyethyleneimine, water-soluble crosslinkable derivatives of a polyvinylamine, and a water-soluble crosslinkable polyurea prepolymer are those described above.

In a preferred embodiment, the prepolymer is water soluble, the fluid composition comprises water and NaCl present in an amount sufficient to increase refractive index differences (delta n) between high and low irradiated areas resulted from a pattern of interference fringes formed between two beams of coherent light.

In another preferred embodiment, the composition comprises aromatic groups associated with the prepolymer and/or the vinylic monomer, wherein the aromatic groups are present in an amount sufficient to increase refractive index differences (delta n) between areas of different polymer densities which are caused by different irradiations resulted from a pattern of interference fringes formed between two beams of coherent light.

The previous disclosure will enable one having ordinary skill in the art to practice the invention. In order to better enable the reader to understand specific embodiments and the advantages thereof, reference to the following examples is suggested.

EXAMPLE 1

Synthesis of Polyvinylalcohol Macromers (Macromers 1-5)

1. 45 ml ultra pure water and 20 ml DMSO are added in a 250 ml three neck bottom flask, equipped with thermometer and heated to 60° C. on a water bath.
2. About 9.7 g of Mowiol™ 383 (which is available from Hoechst Celanese Corp. NC) is added to the water. The mixture is heated to 90° C. under stirring until a clear solution is obtained. The solution is allowed to cool to 25° C.
3. An amount of an aromatic material (listed and specified in Table 1) is added into the solution. The reaction mixture is heated to 60° C. until homogeneous and cool again to the room temperature.
4. About 0.8 g of N-acrylamido acetaldehyde dimethyl acetal is added, followed by 6.467 g (5.43 ml) HCl (37%) quickly poured into solution. Stirring for 7 hours. (N-acrylamido acetaldehyde dimethyl acetal is obtained by the reaction of aminoacetaldehyde dimethylacetal (Aldrich) with methacryloyl chloride (Aldrich). The reaction is described in example 1a of U.S. Pat. No. 5,508,317A.
5. The solution adjusted to pH 7 with NaOH (15%). A color changed accompanies the transition from acid to neutral solution for most of reaction list below.
6. The polymer is precipitated in ca. 900 ml of acetone under stirring.
7. The mixture is then filtered and the filtrate dispersed twice into a 150 ml mixture of water acetone (3/10% v:v) under stirring for 30 minutes. The filtrate is washed with 100 ml acetone and dried overnight at 40° C.

TABLE 1

| Macromer | Amount of aromatic group containing component |
|---|---|
| 1 | 3,5-Dihydroxybenzaldehyde (0.51 g) |
| 2 | 3,5-Dihydroxybenzaldehyde (0.51 g) |
| 3 | 3,5-Dihydroxybenzaldehyde (1.00 g) |
| 4 | 3,5-Dimethoxybenzaldehyde (1.00 g) |
| 5 | 3,5-diiodosalicylaldehyde (1.00 g) |

Formulations are prepared from macromers 1-5 to have a composition specified in Table 2. An amount of each formulations is placed between two quartz slides separated by 50 microns with spacers and holograms are recorded. Percent efficiencies of the 50 microns thick holograms are determined by dividing the energy of the selected mode by the energy of the incident light.

TABLE 2

Formulation compositions and corresponding percent efficiency

| | Crosslinkable fluid material | | | | |
|---|---|---|---|---|---|
| Experiment | Macromer (1.5 g) | Irgacure 2959 [mg] | $H_2O$ [g] | DMSO [g] | Efficiency [%] |
| 001 | 1 | 15 | 3.5 | — | 98 |
| 002 | 2 | 15 | 3.5 | — | 98 |
| 003 | 1 | 20 | 3.5 | — | 96 |
| 004 | 2 | 20 | 3.5 | — | |
| 005 | 1 | 30 | 3.5 | — | 98 |
| 006 | 2 | 30 | 3.5 | — | |
| 007 | 3 | 15 | 2.5 | 1.0 | 88 |
| 008 | 3 | 30 | 2.5 | 1.0 | 97 |
| 009 | 4 | 30 | 3.0 | 1.5 | 88 |
| 010 | 5 | 15 | 3.0 | 0.5 | 70 |
| 011 | 5 | 20 | 3.0 | 0.5 | 70 |
| 012 | 5 | 30 | 3.0 | 0.5 | 79 |

Blind tests

| Experiments | Nelfilcon* [g] | Irgacure 2959 [mg] | Water [g] | Efficiency [%] |
|---|---|---|---|---|
| 013 | 5 | 7.5 | — | 30 |
| 014 | 1.5 | 5 | 3.5 | 30 |
| 015 | 1.5 | 10 | 3.5 | 10 |
| 016 | 1.5 | 15 | 3.5 | 60 |

Experimental results show that an efficiency of up to 98% can be obtained when using a macromer containing aromatic groups. Comparing with blind tests (nelfilcon, a macromer without aromatic group), a substantial increase in efficiency (70% or higher) can be achieved by using a macromer containing aromatic groups. It is believed that when the amount of aromatic groups present in a macromer is sufficient high, one can enhance refractive index difference (delta n) between area of different polymer densities which are generated by different irradiation resulted from a pattern of interference fringes.

EXAMPLE 2

Dried PVA is obtained by precipitation of Nelficon formulation twice into a 150 ml mixture of water acetone (3/10% v:v) under stirring for 30 minutes. The filtrate is washed with 100 ml acetone and dried overnight at 40° C.

Nelfilcon macromer or dried PVA macromers are formulated with additional salt, photoinhibitor and solvent according to compositions specified in Tables 3-4.

The resulting formulations are placed between two quartz slides separated by 50 microns with spacers and holograms are recorded.

Percent efficiencies of the 50 microns thick holograms are determined by dividing the energy of the selected mode by the energy of the incident light.

TABLE 3

Formulations based on Nelfilcon containing various amounts of NaCl and photoinitiator

| Formulation | Nelfilcon* [g] | NaCl [g] | Irgacure 2959 [mg] | Efficiency** [%] |
|---|---|---|---|---|
| 2059 | 5 | 0.025 | — | 40 |
| 2068 | 5 | 0.05 | — | 23 |
| 2069 | 5 | 0.25 | — | 65 |
| 2085-1 | 5 | 0.25 | 20 | 70 |
| 2110 | 5 | 0.25 | 15 | 35 |
| 2111 | 5 | 0.25 | 10 | 30 |
| 2112 | 5 | 0.25 | 5 | 30 |
| 2113 | 5 | 0.25 | 2.5 | 37 |

*amount of component normalized to 5 g Nelfilcon
**highest value achieved at 50 μm thick sample

TABLE 4

Example formulation based on dried PVA containing various amounts of NaCl and photoinitiator

| Formulation | PVA* [g] | NaCl [g] | Irgacure 2959 [mg] | Water [g] | DMSO [g] | Efficiency** [%] |
|---|---|---|---|---|---|---|
| 2102 | 1.5 | 0.25 | 5 | 3.5 | — | 70 |
| 2103 | 1.5 | 0.25 | 7.5 | 3.5 | — | 80 |
| 2101 | 1.5 | 0.25 | 10 | 3.5 | — | 90 |
| 2070 | 1.5 | 0.25 | 15 | 3.5 | — | 70 |
| 2107 | 1.5 | 0.25 | 17 | 3.5 | — | 70 |
| 2085-2 | 1.5 | 0.25 | 20 | 3.5 | — | 95 |
| 2086 | 1.5 | 0.25 | 25 | 3.5 | — | 75 |
| 2087 | 1.5 | 0.35 | 30 | 3.5 | — | 83 |
| 2088 | 1.5 | 0.35 | 15 | 3.5 | — | 81 |
| 2089 | 1.5 | 0.45 | 15 | 3.5 | — | 95 |
| 2090 | 1.5 | 0.45 | 20 | 3.5 | — | 95 |
| 2109 | 1.5 | 0.5 | 15 | 3.5 | — | 98 |
| 2104 | 1.5 | 0.25 | 10 | 3.5 | 1 | |
| 2131 | 1.5 | 0.35 | 5 | 3.5 | — | 83 |
| 2132 | 1.5 | 0.35 | 7.5 | 3.5 | — | 87 |
| 2133 | 1.5 | 0.35 | 10 | 3.5 | — | 92 |
| 2134 | 1.5 | 0.45 | 5 | 3.5 | — | |
| 2135 | 1.5 | 0.45 | 7.5 | 3.5 | — | 62 |
| 2136 | 1.5 | 0.45 | 10 | 3.5 | — | 98 |
| blind | | | | | | |
| 2137 | 1.5 | — | 5 | 3.5 | — | 40 |
| 2138 | 1.5 | — | 10 | 3.5 | — | 20 |
| 2139 | 1.5 | — | 15 | 3.5 | — | 70 |

*amount of component normalized to 1.5 g dried PVA
**highest value achieved at 50 μm thick sample Control experiments (blind tests) show that the efficiency of a 50 microns thick hologram made from a formulation without additional NaCl is from about 40% to about 50%. In the presence of additional NaCl in a formulation, the efficiency of a 50 microns thick hologram made from that formulation increases from 40-50% up to 98%, with an average of about 80%. The efficiency of a 50 microns thick hologram made from a formulation increases with NaCl concentration in that formulation. Results do not show any clear trend about the effects of initiator on the efficiency of a 50 microns thick hologram.

Where other salts are used in experiments, no significant Increase in efficiency, compared to blind tests, are observed.

Although various embodiments of the invention have been described using specific terms, devices, and methods, such description is for illustrative purposes only. The words used are words of description rather than of limitation. It is to be understood that changes and variations may be made by those skilled in the art without departing from the spirit or scope of the present invention, which is set forth in the following claims. In addition, it should be understood that aspects of the various embodiments may be Interchanged either in whole or in part. Therefore, the spirit and scope of the appended claims should not be limited to the description of the preferred versions contained therein.

What is claimed is:

1. A method for making a biocompatible sensor containing a reflection hologram, comprising the steps of:
    introducing a crosslinkable and/or polymerizable fluid material into a cavity formed by a mold, wherein the crosslinkable and/or polymerizable fluid material comprises at least a molecular sensing moiety which can interact or react with an analyte of interest to provide an optical signal which is indicative of a change in one or more optical properties of the reflection hologram, wherein the mold has a first mold half defining a first molding surface and a second mold half defining a second molding surface, wherein said first mold half and said second mold half are configured to receive each other such that the cavity is formed between said first molding surface and said second molding surface, wherein the second mold half has, on or behind the second molding surface, a mirror to reflect incident light coming from the first molding surface; and
    producing and recording a pattern of interference fringes while polymerizing/crosslinking said crosslinkable and/or polymerizable fluid material in the cavity by directing an incident beam of coherent light through the first molding surface to said crosslinkable and/or polymerizable fluid material and to said mirror, wherein the incident beam and a beam reflected by the mirror form said pattern while polymerizing/crosslinking said crosslinkable and/or polymerizable fluid material to form the biocompatible sensor, whereby said pattern is recorded in said biocompatible sensor to form the reflection hologram.

2. The method of claim 1, further comprising the step of partially crosslinking and/or polymerizing the crosslinkable and/or polymerizable fluid material by actinic irradiation, before the step of producing and recording.

3. The method of claim 1, wherein the crosslinkable and/or polymerizable fluid material comprises a water-soluble prepolymer.

4. The method of claim 3, wherein the water-soluble prepolymer is selected from the group consisting of: a water-soluble crosslinkable poly(vinyl alcohol) prepolymer; a water-soluble vinyl group-terminated polyurethane; a water-soluble crosslinkable polyurea prepolymer; a crosslinkable polyacrylamide; a crosslinkable statistical copolymers of vinyl lactam, MMA and a comonomer; a crosslinkable copolymers of vinyl lactam, vinyl acetate and vinyl alcohol; a polyether-polyester copolymer with crosslinkable side chains; a branched polyalkylene glycol-urethane prepolymer; a polyalkylene glycol-tetra(meth)acrylate pre polymer; and a crosslinkable polyallylamine gluconolactone prepolymer, wherein the polyurea prepolymer is obtained by reacting an acryloylchloride or an isocyanate group-containing acrylate or methacrylate with a polymerization product of NH2-terminated polyalkylene glycols and di- or polyisocyanates optionally in the presence of a triamine,
wherein the vinyl group-terminated polyurethane is obtained by reacting an isocyanate-capped polyurethane with an ethylenically unsaturated amine (primary or secondary amine) or an ethylenically unsaturated monohydroxy compound, wherein the isocyanate-capped polyurethane is a copolymerization product of at least one polyalkylene glycol, a compound containing at least 2 hydroxyl groups, and at least one compound with two or more isocyanate groups, wherein the crosslinkable poly(vinyl alcohol) is a polyhydroxyl compound which has a molecular weight of at least about 2000 and comprises from about 0.5 to about 80%, based on the number of hydroxyl groups in the poly(vinyl alcohol), of units of the formula I, I and II, I and III, or I and II and III

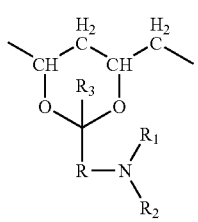

I

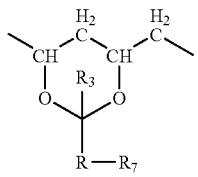

II

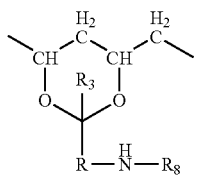

III wherein R is alkylene having up to 12 carbon atoms; $R_1$ is hydrogen or lower alkyl having up to seven carbon atoms; $R_2$ is an olefinically unsaturated, electron-withdrawing, crosslinkable radical having up to 25 carbon atoms; $R_3$ is hydrogen, a $C_1$-$C_6$ alkyl group or a cycloalkyl group; $R_7$ is a primary, secondary or tertiary amino group or a quaternary amino group of the formula $N^+(R')_3X^-$, in which each R', independently of the others, is hydrogen or a $C_1$-$C_4$ alkyl radical and X is a counterion selected from the group consisting of $HSO_4^-$, $F^-$, $Cl^-$, $Br^-$, $I^-$, $CH_3COO^-$, $OH^-$, $BF^-$, and $H_2PO_4^-$; and $R_8$ is the radical of a monobasic, dibasic or tribasic, saturated or unsaturated, aliphatic or aromatic organic acid or sulfonic acid.

5. The method of claim 3, wherein the molecular sensing moiety is a phenyl boronic acid having formula (4), (5), or (6)

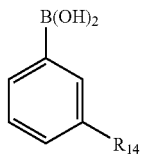

(4)

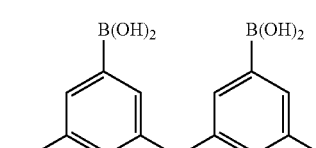

(5)

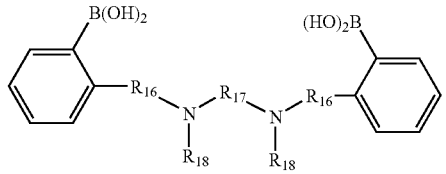

(6)

wherein $R_{14}$ and $R_{18}$, independently of each other, are olefinically unsaturated, crosslinkable radicals; $R_{15}$ and $R_{16}$, independently of each other, are alkylene having up to 12 carbon atoms; and $R_{17}$ is an arylene having 6 to 12 carbon atoms, a saturated bivalent cycloaliphatic group having 6 to 10 carbon atoms, arylenealkylene or alkylenearylene having 7 to 14 carbon atoms or arylenealkylenearylene having 13 to 16 carbon atoms.

6. The method of claim 3, wherein the crosslinkable and/or polymerizable fluid material is an aqueous solution, wherein the aqueous solution includes a low molecular weight additive which exhibit a limited compatibility with a polymer matrix resulted from the crosslinkable and/or polymerizable fluid material, but good compatibility with water, wherein the low molecular weight additive is present in an amount sufficient to increase refractive index differences (delta n) between high and low irradiated areas resulted from the pattern of interference fringes.

7. The method of claim 6, wherein the low molecular weight additive is NaCl.

8. The method of claim 1, wherein the crosslinkable and/or polymerizable fluid material comprises at least one prepolymer and optionally a vinylic monomer, wherein at least one of the prepolymer and the vinylic monomer contains aromatic groups in an amount sufficient to increase refractive index differences (delta n) between areas of different polymer densities which are caused by different irradiations resulted from the pattern of interference fringes.

* * * * *